US008918740B2

(12) United States Patent
Nishiyama

(10) Patent No.: US 8,918,740 B2
(45) Date of Patent: Dec. 23, 2014

(54) IMAGE MANAGEMENT APPARATUS, METHOD, AND COMPUTER-READABLE RECORDING MEDIUM AND CAPSULE ENDOSCOPE SYSTEM

(71) Applicant: Olympus Medical Systems Corp., Tokyo (JP)

(72) Inventor: Takeshi Nishiyama, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/632,475

(22) Filed: Oct. 1, 2012

(65) Prior Publication Data
US 2013/0152020 A1 Jun. 13, 2013

Related U.S. Application Data

(63) Continuation of application No. PCT/JP2012/056131, filed on Mar. 9, 2012.

(30) Foreign Application Priority Data

Mar. 30, 2011 (JP) .................................. 2011-076716

(51) Int. Cl.
*G06F 3/048* (2013.01)
*G06K 9/00* (2006.01)
(Continued)

(52) U.S. Cl.
CPC ............ *G06F 19/321* (2013.01); *G06T 7/0012* (2013.01); *G06T 19/00* (2013.01);
(Continued)

(58) Field of Classification Search
CPC ... G06F 19/322; G06F 19/325; G06F 19/321; G06F 19/30

USPC .......... 715/812, 835; 382/128, 182, 224–228; 600/118
See application file for complete search history.

(56) References Cited

U.S. PATENT DOCUMENTS 4,906,940 A * 3/1990 Greene et al. ................. 382/100
6,810,149 B1 * 10/2004 Squilla et al. ................. 382/224
(Continued)

FOREIGN PATENT DOCUMENTS

CN 1777391 A 5/2006
JP 11-132932 A 5/1999
(Continued)

OTHER PUBLICATIONS

O'Sullivan et al., "Task-based annotation and retrieval for image information management", Multimedia Tools and Applications, Aug. 2011, vol. 54, Issue 2, pp. 473-497.*

(Continued)

*Primary Examiner* — Omar Abdul-Ali
*Assistant Examiner* — Andrew Tank
(74) *Attorney, Agent, or Firm* — Scully, Scott, Murphy & Presser, P.C.

(57) ABSTRACT

An image management apparatus includes: a storage unit that stores a plurality of types of additional information assigned to a plurality of images; a calculation unit that calculates a feature quantity of each of the images; an extracting unit that extracts, based on the feature quantity, additional information of the plurality of types of additional information; a control unit that generates one or more icons corresponding to the one or more types of additional information and displays the icons on a screen; an input unit that receives input according to a user's operation; a selecting unit that selects an image according to the signal; and an assigning unit that assigns to the selected image, when input of an operation signal associating the image selected by the image selecting unit with an icon selected by the user is received, additional information corresponding to the icon associated with the selected image.

14 Claims, 26 Drawing Sheets

(51) Int. Cl.
*A61B 1/04* (2006.01)
*G06T 7/00* (2006.01)
*G06T 19/00* (2011.01)
*A61B 1/00* (2006.01)
*G06F 19/00* (2011.01)

(52) U.S. Cl.
CPC ....... *G06T 2200/24* (2013.01); *G06T 2219/004* (2013.01); *A61B 1/00041* (2013.01); *G06T 2207/30028* (2013.01); *A61B 1/0005* (2013.01); *A61B 1/00009* (2013.01); *A61B 1/041* (2013.01); *G06T 2207/10068* (2013.01)
USPC ............ 715/835; 715/812; 382/128; 600/118

(56) References Cited

U.S. PATENT DOCUMENTS

| | | | |
|---|---|---|---|
| 7,130,457 B2 * | 10/2006 | Kaufman et al. | 382/128 |
| 7,283,857 B1 | 10/2007 | Fallon et al. | |
| 7,783,135 B2 * | 8/2010 | Gokturk et al. | 382/305 |
| 8,051,386 B2 * | 11/2011 | Rosander et al. | 715/810 |
| 8,259,995 B1 * | 9/2012 | Schendel et al. | 382/103 |
| 8,340,437 B2 * | 12/2012 | Abramoff et al. | 382/224 |
| 8,446,465 B2 * | 5/2013 | Ambor et al. | 348/65 |
| 8,463,741 B2 * | 6/2013 | Ehlke et al. | 707/608 |
| 8,467,583 B2 * | 6/2013 | Smith et al. | 382/128 |
| 2002/0171669 A1 * | 11/2002 | Meron et al. | 345/619 |
| 2004/0249291 A1 * | 12/2004 | Honda et al. | 600/476 |
| 2009/0131746 A1 * | 5/2009 | Seo et al. | 600/101 |
| 2010/0269064 A1 * | 10/2010 | Lobregt et al. | 715/810 |
| 2011/0131528 A1 | 6/2011 | Nakamura | |
| 2011/0218397 A1 | 9/2011 | Nishiyama et al. | |
| 2011/0249952 A1 | 10/2011 | Taniguchi | |
| 2012/0316421 A1 * | 12/2012 | Kumar et al. | 600/407 |

FOREIGN PATENT DOCUMENTS

| | | |
|---|---|---|
| JP | 2002-531198 A | 9/2002 |
| JP | 2007-330374 A | 12/2007 |
| JP | 2009-233177 A | 10/2009 |
| JP | 2011-25056 A | 2/2011 |
| WO | WO 2010/109726 A1 | 9/2010 |
| WO | WO 2010/113479 A1 | 10/2010 |
| WO | WO 2011/005865 A2 | 1/2011 |
| WO | WO 2011/013475 A1 | 2/2011 |

OTHER PUBLICATIONS

Rubin et al., "Annotation and Image Markup: Accessing and Interoperating with the Semantic Content in Medical Imaging", Intelligent Systems IEEE, Jan.-Feb. 2009, vol. 24, Issue 1, pp. 57-65.*
Extended Supplementary European Search Report dated Nov. 7, 2013 in European Patent Application No. 12763147.1.
Chinese Office Action dated Jan. 28, 2014 in corresponding Chinese Patent Application No. 201280003184.6.

* cited by examiner

IMAGE MANAGEMENT APPARATUS, METHOD, AND COMPUTER-READABLE RECORDING MEDIUM AND CAPSULE ENDOSCOPE SYSTEM

CROSS-REFERENCE TO RELATED APPLICATIONS

This application is a continuation of PCT international application Ser. No. PCT/JP2012/056131 designating the United States and filed on Mar. 9, 2012 which claims the benefit of priority from Japanese Patent Applications No. 2011-076716, filed on Mar. 30, 2011, and the entire contents of the Japanese patent application and the PCT international application are incorporated herein by reference.

BACKGROUND OF THE INVENTION

1. Field of the Invention

The present invention relates to: an image management apparatus, a method, and a computer-readable recording medium that display in-vivo images obtained by a capsule endoscope introduced inside a subject; and a capsule endoscope system.

2. Description of the Related Art

Upon examination of a subject using a capsule endoscope that is introduced inside the subject and captures images inside the body, a group of in-vivo images obtained by the capsule endoscope are observed as a pseudo moving image or a list of still images, and an operation of selecting those having abnormal findings is performed. This operation is called observation of images.

Generally, when an in-vivo image with an abnormal finding is found, a user (for example, a medical doctor) performs management by assigning additional information such as a label to the image, so that the in-vivo image is able to be extracted upon later diagnosis. Conventionally, this assignment of labels has been done by inputting text for each in-vivo image. However, since a group of in-vivo images that are captured in one examination has, for example, about 60,000 images (corresponding to about eight hours), work load for the assignment of labels is very large.

Thus, a technique is demanded which allows easy assignment of a label to each in-vivo image without performing an operation of inputting text or the like one by one. For example, in Japanese Laid-open Patent Publication No. 11-132932, classification of images by selecting images on a screen by using, e.g., a method of dragging the images with a mouse, and dropping the images on icons of classified items, is disclosed.

SUMMARY OF THE INVENTION

An image management apparatus according to an aspect of the present invention includes: a storage unit that stores a plurality of types of additional information assigned to a plurality of images; a calculation unit that calculates a feature quantity of each of the plurality of images; an additional information extracting unit that extracts, based on the feature quantity, one or more types of additional information of the plurality of types of additional information; a display control unit that generates one or more icons corresponding to the one or more types of additional information and causes the generated icons to be displayed on a screen; an input unit that receives input of a signal according to a user's operation; an image selecting unit that selects, from the plurality of images, an image according to the signal received by the input unit; and an additional information assigning unit that assigns to the selected image, when input of an operation signal associating the image selected by the image selecting unit with an icon selected from the one or more icons by the user is received by the input unit, additional information corresponding to the icon associated with the selected image.

An image management method according to another aspect of the present invention includes: calculating a feature quantity of each of a plurality of images; extracting, from a plurality of types of additional information to be assigned to the plurality of images and stored beforehand in a storage unit, one or more types of additional information, based on the feature quantity; generating and displaying on a screen one or more icons corresponding to the one or more types of additional information; receiving input of a signal according to a user's operation; selecting, from the plurality of images, an image according to the signal received via the input; and assigning to the selected image, when input of an operation signal associating the image selected in the selecting of the image with an icon selected from the one or more icons by the user is received, additional information corresponding to the icon associated with the image.

A computer-readable recording medium according to still another aspect of the present invention, has an executable program recorded thereon, the program instructing a processor to perform: calculating a feature quantity of each of a plurality of images; extracting, from a plurality of types of additional information to be assigned to the plurality of images and stored beforehand in a storage unit, one or more types of additional information, based on the feature quantity; generating and displaying on a screen one or more icons corresponding to the one or more types of additional information; receiving input of a signal according to a user's operation; selecting, from the plurality of images, an image according to the signal received via the input; and assigning to the selected image, when input of an operation signal associating the image selected in the selecting of the image with an icon selected from the one or more icons by the user is received, additional information corresponding to the icon associated with the image.

A capsule endoscope system according to yet another aspect of the present invention includes: a capsule endoscope that is introduced inside a body of a subject, performs imaging, and generates image data corresponding to in-vivo images of the subject; a receiving device that receives the image data generated by the capsule endoscope via wireless communications with the capsule endoscope; and an image management apparatus that receives and manages the image data received by the receiving device, wherein the image management apparatus includes: a storage unit that stores a plurality of types of additional information assigned to a plurality of images; a calculation unit that calculates a feature quantity of each of the plurality of images; an additional information extracting unit that extracts, based on the feature quantity, one or more types of additional information of the plurality of types of additional information; a display control unit that generates one or more icons corresponding to the one or more types of additional information and causes the generated icons to be displayed on a screen; an input unit that receives input of a signal according to a user's operation; an image selecting unit that selects, from the plurality of images, an image according to the signal received by the input unit; and an additional information assigning unit that assigns to the selected image, when input of an operation signal associating the image selected by the image selecting unit with an icon selected from the one or more icons by the user is received by the input unit, additional information corresponding to the icon associated with the selected image.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an image management apparatus, a method, and a computer-readable recording medium, and a capsule endoscope system according to embodiments of the present invention will be described with reference to the drawings. In the description below, while a system including a capsule endoscope that is introduced inside a subject and captures in-vivo images will be exemplified as one example, the present invention is not limited by this embodiment.

First Embodiment

Figure 1:
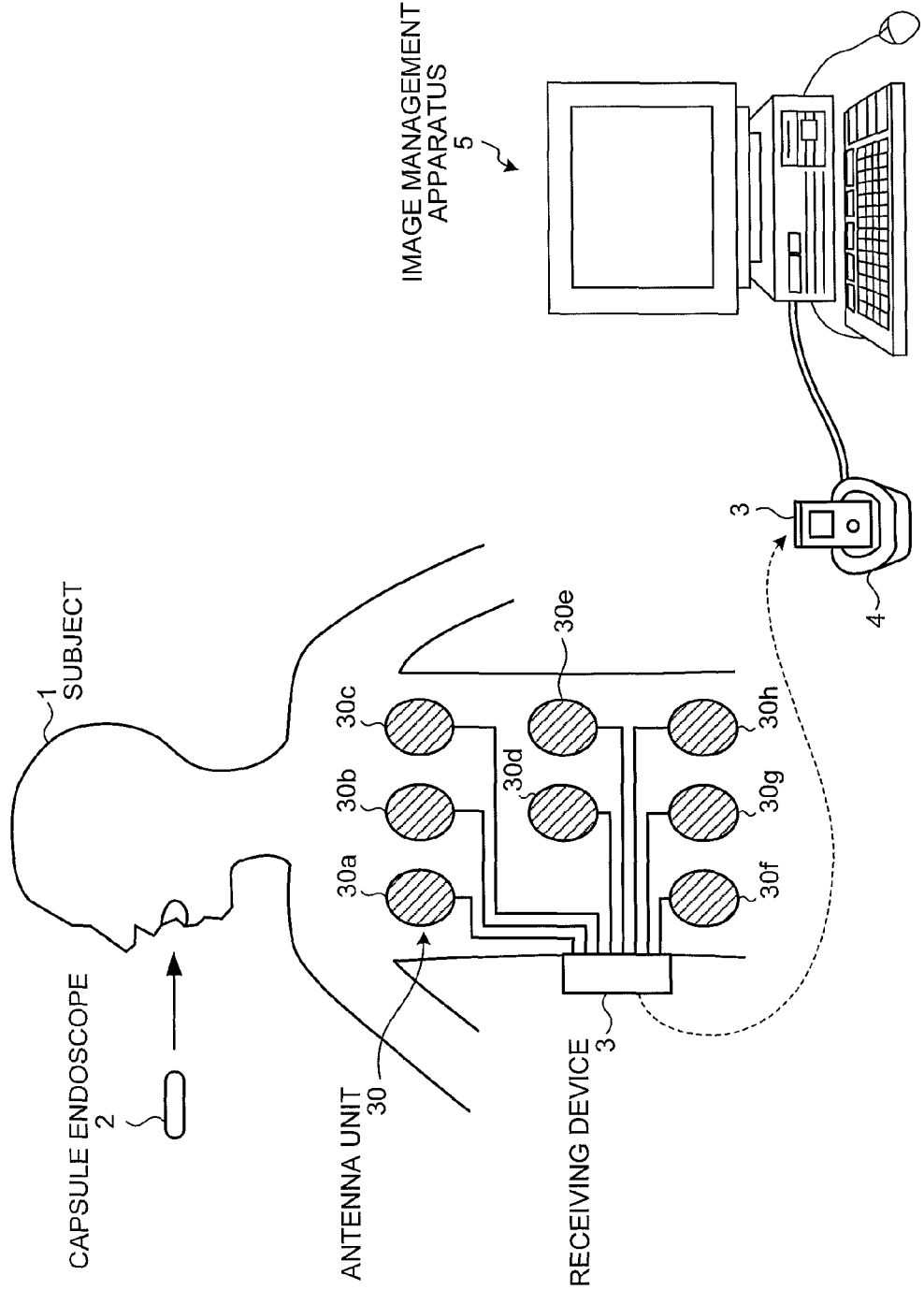
FIG. 1 is a schematic diagram that illustrates a configuration of a capsule endoscope system according to a first embodiment of the invention.

FIG. 1 is a schematic diagram that illustrates a configuration of a capsule endoscope system according to a first embodiment of the invention. The endoscope system illustrated in FIG. 1 includes: a capsule endoscope 2 that is introduced inside a subject 1, performs imaging, and wirelessly transmits obtained image data; a receiving device 3 that receives the image data wirelessly transmitted from the capsule endoscope 2; and an image management apparatus 5 that manages in-vivo images that are based on the image data transferred from the receiving device 3 through a cradle 4.

The capsule endoscope 2 has, built therein: an illumination device that illuminates inside the subject 1; a condenser lens that condenses reflected light from the inside of the subject 1; an imaging device such as a CCD that converts received light into an electric signal (imaging signal); an IC that constitutes a signal processing unit that processes the imaging signal obtained by the imaging device; and various components such as a transmission wireless antenna and the like. After being swallowed from the mouth of the subject 1, the capsule endoscope 2 sequentially captures images of living body parts (esophagus, stomach, small intestine, large intestine, and the like) at predetermined time intervals (for example, at 0.5-second intervals) while moving inside the digestive tract of the subject 1 by peristaltic motion of organs or the like. Then, image data are generated by performing predetermined signal processing for the imaging signal that is obtained by image-capturing and the image data are sequentially transmitted wirelessly together with related information of the image data to the receiving device 3. In the related information, identification information (for example, a serial number) or the like that is assigned for individually identifying the capsule endoscope 2 is included.

The receiving device 3 receives the image data and the related information that are wirelessly transmitted from the capsule endoscope 2 through an antenna unit 30 that includes a plurality of (eight in FIG. 1) receiving antennas 30a to 30h. The receiving antennas 30a to 30h, for example, are each realized using a loop antenna and are arranged at predetermined positions (for example, positions corresponding to organs inside the subject 1 that are on a passage route of the capsule endoscope 2) on an out-of-body surface of the subject 1.

The receiving device 3 is carried by the subject 1 while image-capturing is being performed by the capsule endoscope 2 (for example, until the capsule endoscope 2 is discharged after being introduced from the mouth of the subject 1 and passing through the digestive tract). Meanwhile, the receiving device 3 further adds related information such as reception strength information, reception time information, and the like of the receiving antennas 30a to 30h to the image data received through the antenna unit 30 and stores the image data and the related information in a built-in memory. After the image-capturing by the capsule endoscope 2 is finished, the receiving device 3 is removed from the subject 1 and is set in the cradle 4 that is connected to a USB port or the like of the image management apparatus 5. Thereby, the receiving device 3 is connected to the image management apparatus 5, and the image data and the related information that are stored in the built-in memory are transferred to the image management apparatus 5.

Fetching of the image data and the like into the image management apparatus 5 is not limited to the method that is performed through the cradle 4. For example, if image data and the like that are stored in a server are processed, the image data and the like may be fetched through a communication device that is connected to the server, and if image data and the like that are recorded in a portable recording medium such as a CD-R or a DVD-R are processed, the image data and the like may be read from the recording medium by a reading device that is built in the image management apparatus 5. Alternatively, a medical observation device may be connected to the image management apparatus 5, and image data and the like may be fetched directly from the medical observation device.

Figure 2:
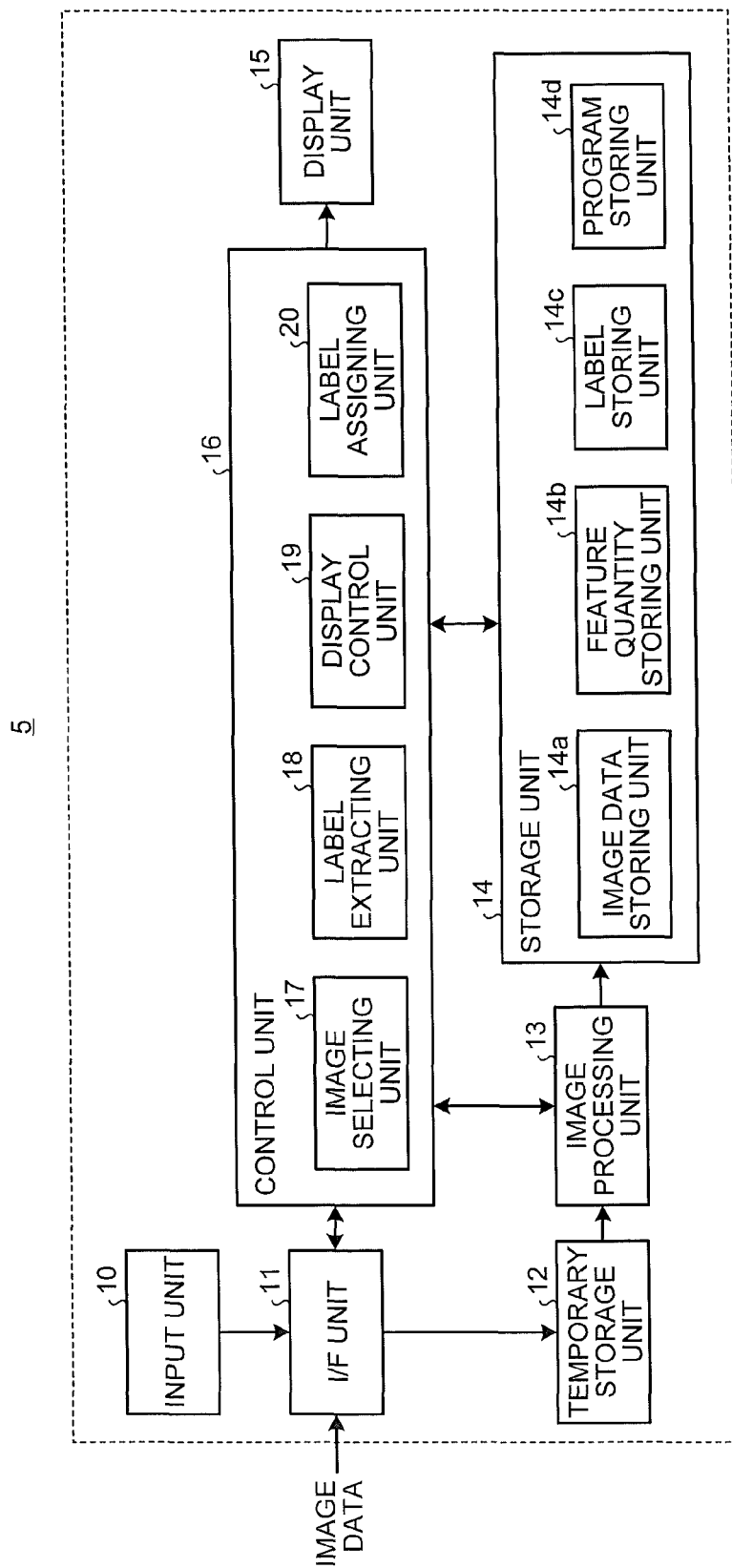
FIG. 2 is a block diagram that illustrates a configuration of an image management apparatus illustrated in FIG. 1.

FIG. 2 is a block diagram that illustrates a configuration of the image management apparatus according to the first embodiment of the invention. The image management apparatus 5 illustrated in FIG. 2 includes an input unit 10, an interface (I/F) unit 11, a temporary storage unit 12, an image processing unit 13, a storage unit 14, a display unit 15, and a control unit 16 that controls such units.

The input unit 10 is realized by an input device such as a keyboard, a mouse, a touch panel, or various kinds of switches. The input unit 10 receives input of an operation signal in accordance with a user's operation and inputs the operation signal to the control unit 16 through the interface unit 11.

The interface unit 11 includes a connection port to an external device (a reading device or the like that reads image data from a portable recording medium) such as a USB port and receives input or the like of various instructions and information input through the input unit 10 or signals representing the image data and their related information that are input through the USB port or the like.

The temporary storage unit 12 is realized by a volatile memory such as a DRAM or an SRAM and temporarily stores the image data and their related information that are input through the interface unit 11. Alternatively, a recording medium such as an HDD, an MO, a CD-R, or a DVD-R and a driving device that drives the recording medium may be provided instead of the temporary storage unit 12, and the image data input from the interface unit 11 may be stored in the recording medium for the time being.

The image processing unit 13 is a calculation unit that performs image processing such as white balance processing, demosaicing, color conversion, density conversion (gamma conversion or the like), smoothing (noise elimination or the like), or sharpening (edge highlighting or the like) on the image data stored in the temporary storage unit 12 to generate a series of in-vivo images, and calculates a feature quantity of each in-vivo image. As the feature quantity that is calculated by the image processing unit 13, a luminance value, a color feature quantity (RGB values, a hue value, or the like), a structural feature quantity (an edge amount or the like), a distribution of the feature quantity, or the like is used.

The storage unit 14 is realized by a semiconductor memory such as a flash memory, a RAM, or a ROM, or a recording medium such as an HDD, an MO, a CD-R, or a DVD-R, and a driving device or the like that drives the recording medium. The storage unit 14 stores a program for causing the image management apparatus 5 to operate and execute various functions and data (dictionary data or the like) used during execution of the program. More specifically, the storage unit 14 includes: an image data storing unit 14a that stores image data corresponding to in-vivo images for which image processing has been performed; a feature quantity storing unit 14b that stores the feature quantities of the in-vivo images that are calculated by the image processing unit 13; a label storing unit 14c that stores labels of a plurality of types that are additional information assigned to the in-vivo images; and a program storing unit 14d that stores an image management program that causes the control unit 16 to execute a series of processes for assigning labels to the in-vivo images and managing them.

The image data storing unit 14a may store in-vivo images as a time series, or classify the in-vivo images into a plurality of groups and store them according to control of the control unit 16. For example, if boundaries between organs (a boundary between esophagus and stomach, a boundary between stomach and small intestine, a boundary between small intestine and large intestine, and the like) upon arranging the in-vivo images as a time series have been determined based on color feature quantities calculated by the image processing unit 13, the image data storing unit 14a classifies the series of in-vivo images into organ groups in accordance with the boundaries of the organs and stores them. Here, the boundaries of the organs may be based on spatial indices such as boundaries upon arranging the in-vivo images in order of distance (hereinafter, referred to as movement distances) representing a length of the digestive tract calculated from a predetermined passage position (for example, the entrance of the esophagus or the entrance of the stomach) when the capsule endoscope 2 moves inside the subject 1 or boundaries upon arranging the in-vivo images based on a track of the capsule endoscope 2 moved inside the subject 1. This track of the capsule endoscope 2 is obtained, for example, by estimating, based on the related information (the reception strength information and the reception time information) of the image data, the position of the capsule endoscope 2 at the time when each in-vivo image is obtained and connecting such positions together.

The labels that are stored by the label storing unit 14c are information formed of keywords medically having meanings, and names of diseases (for example, stomach ulcer, stomach cancer, and ulcerative colitis), symptom names of lesions (for example, hemorrhage, angiodysplasia, inflammation, ulcer, polyp, and cancer) or the like are included. Alternatively, as the labels, organ labels (for example, stomach, small intestine, and large intestine) that are classified based on color feature quantities may be used.

The display unit 15 is realized by a display device such as a CRT display, a liquid crystal display, or an EL display. The display unit 15 displays in-vivo images and the like on a screen in a predetermined format under the control of the control unit 16.

The control unit 16 is realized by hardware such as a CPU, and by reading various programs that are stored in the program storing unit 14*d*, performs instruction, data transfer, or the like to the elements of the image management apparatus 5 in accordance with image data and various operation signals input through the interface unit 11, and integrally controls the overall operation of the image management apparatus 5. More specifically, the control unit 16 includes an image selecting unit 17, a label extracting unit 18, a display control unit 19, and a label assigning unit 20.

The image selecting unit 17 selects an in-vivo image from a plurality of in-vivo images corresponding to the image data stored in the image data storing unit 14*a* in accordance with a signal input from the input unit 10.

The label extracting unit 18 extracts, based on the feature quantities that are stored in the feature quantity storing unit 14*b*, one or more kinds of labels as candidates for a label to be assigned to the in-vivo image that is selected by the image selecting unit 17 from the plurality of kinds of labels stored in the label storing unit 14*c*. More specifically, the label extracting unit 18 determines an organ that corresponds to the selected in-vivo image and extracts lesion labels that may occur in each organ. For example, if the selected in-vivo image corresponds to the stomach, an ulcer label, an inflammation label, a hemorrhage label, and a cancer label are extracted. In addition, if the selected in-vivo image corresponds to the small intestine, the hemorrhage label, an angiodysplasia label, and a tumor label are extracted. Furthermore, if the selected in-vivo image corresponds to the large intestine, the hemorrhage label, the cancer label, and a polyp label are extracted.

The label extracting unit 18 may determine a corresponding organ based on the time (image captured time) at which the selected in-vivo image is obtained or determine the corresponding organ based on the feature quantity of the selected in-vivo image. Alternatively, the label extracting unit 18 may determine the corresponding organ based on the movement distance of the capsule endoscope 2 that corresponds to the selected in-vivo image or determine the corresponding organ based on the track of the capsule endoscope 2 that has obtained the selected in-vivo image. Furthermore, an input field in which a user is able to input organ information may be provided on an image observation screen (described later) displayed on the display unit 15, and the label extracting unit 18 may determine the corresponding organ based on the organ information that is input in the input field according to a user's determination.

The display control unit 19 generates, based on the image data and the other various kinds of information that are stored in the image data storing unit 14*a*, a screen on which in-vivo images and the like are arranged in a predetermined format, and causes the display unit 15 to display the generated screen. For example, the display control unit 19 generates icons for a label box, the icons corresponding to lesion labels that are extracted by the label extracting unit 18 and causes the display unit 15 to display the icons.

When a signal associating the in-vivo image selected by the image selecting unit 17 with an icon of a label box that is displayed on the display unit 15 is input from the input unit 10, the label assigning unit 20 assigns the label that corresponds to the associated icon to the selected in-vivo image.

Such an image management apparatus 5, for example, is realized by a workstation or a personal computer.

Figure 3:
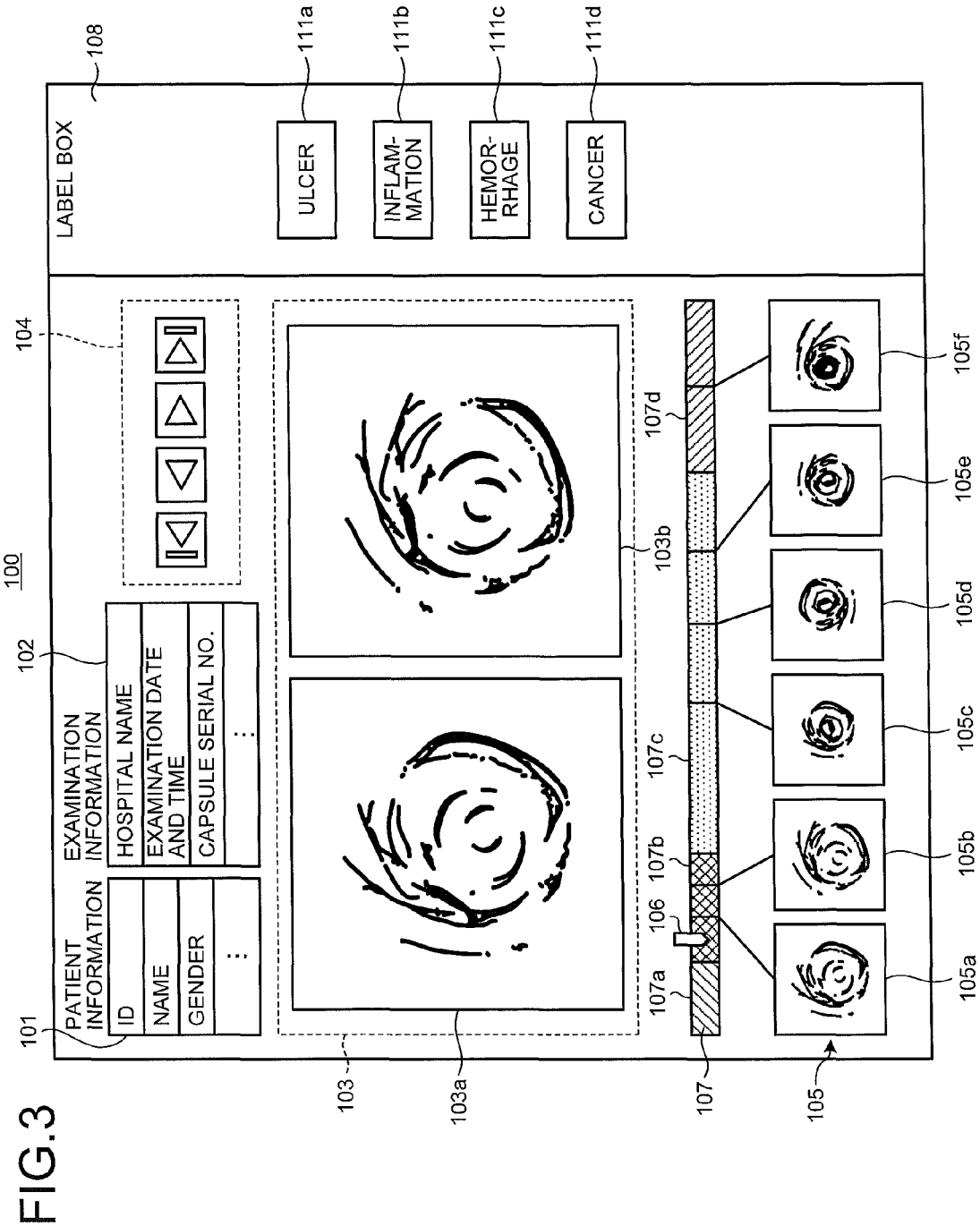
FIG. 3 is a schematic diagram that illustrates a display example of an image observation screen according to the first embodiment.
Figure 4:
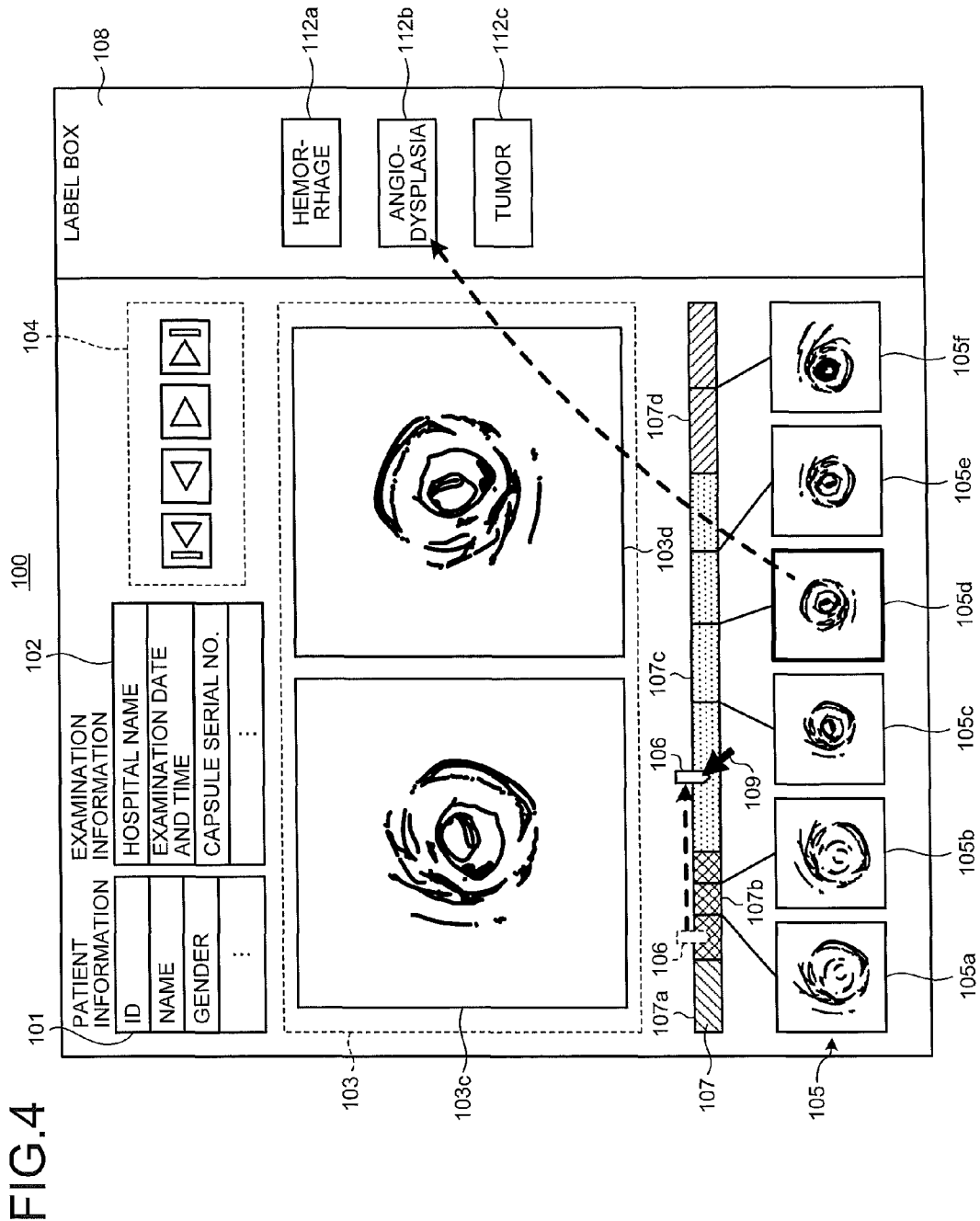
FIG. 4 is a schematic diagram that illustrates a display example of an image observation screen according to the first embodiment.
Figure 5:
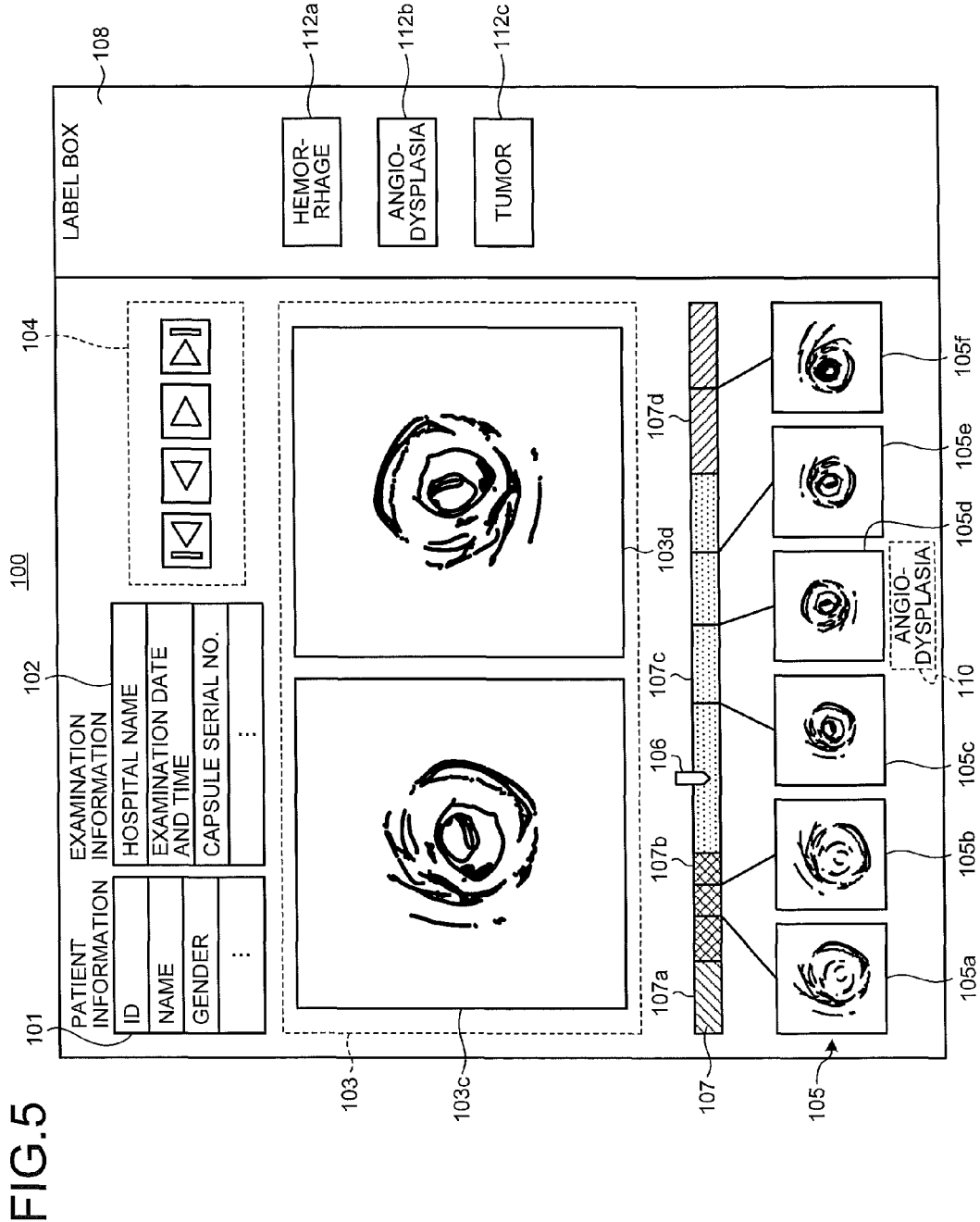
FIG. 5 is a schematic diagram that illustrates a display example of an image observation screen according to the first embodiment.

Next, operations of the image management apparatus 5 will be described with reference to FIGS. 3 to 5. FIGS. 3 to 5 are schematic diagrams that illustrate display examples of an image observation screen that is displayed on the display unit 15.

An image observation screen 100 illustrated in FIG. 3 includes: a patient information area 101 in which identification information of a subject 1 that is a patient is displayed; an examination information area 102 in which identification information of an examination that is performed on the subject 1 is displayed; a main display area 103 in which a series of in-vivo images are sequentially played; a group 104 of play operation buttons that receive input of play operations for in-vivo images 103*a* and 103*b* that are displayed on the main display area 103; a thumbnail area 105 in which reduced images 105*a*, 105*b*, and so on, which are in-vivo images having image sizes that have been reduced, are displayed as thumbnails; a time bar 107 that represents an index of time (for example, image captured time) that corresponds to a series of in-vivo images; a slider 106 that indicates a point on the time bar 107; and a label box display area 108 in which icons 111*a* to 111*d* of a label box that correspond to lesion labels assigned to the in-vivo images are displayed.

The time bar 107 is a scale that corresponds to time until the capsule endoscope 2 is discharged after being introduced inside the subject 1 and is displayed with different colors for different organs correspondingly with the image captured time (in FIG. 3, a difference in color is represented by a difference in pattern). More specifically, for example, areas 107*a*, 107*b*, 107*c*, and 107*d* on the time bar 107 correspond to the esophagus, the stomach, the small intestine, and the large intestine, respectively. The image captured time represents time that has elapsed from the time at which the capsule endoscope 2 is introduced inside the subject 1. The slider 106 designates a point on the time bar 107 that corresponds to the in-vivo image that is being displayed in the main display area 103.

Instead of displaying the time bar 107, a bar that represents an index of space (for example, an imaging spot) that corresponds to a series of in-vivo images may be displayed. For example, a spatial index may be used such as a distance bar that represents a length of the digestive tract calculated from a predetermined passage position (for example, the entrance of the esophagus or the entrance of the stomach) upon movement of the capsule endoscope 2 inside the subject 1 or a capsule track diagram drawing the track of movement of the capsule endoscope 2. In addition, the slider 106 may represent a point on the distance bar or the capsule track diagram.

In the thumbnail area 105, for example, captured images of in-vivo images selected by a pointer operation in the main display area 103 are displayed reduced. In FIG. 3, the reduced images 105*a*, 105*b*, ... are displayed line-connected to points on the time bar 107, which represent their image captured times.

In the label box display area 108, icons according to an organ that corresponds to the area in which the point (corresponding to the image captured times of the in-vivo images 103*a* and 103*b*) designated by the slider 106 is included are displayed. For example, in FIG. 3, since the slider 106 designates within the area 107b that corresponds to the stomach, an icon 111a representing ulcer, an icon 111b representing inflammation, an icon 111c representing hemorrhage, and an icon 111d representing cancer are displayed in the label box display area 108 in correspondence with the lesion labels related to the stomach.

In FIG. 3, although two in-vivo images 103a and 103b are displayed in the main display area 103, the number of images that are main-displayed may be one or three or more. In addition, the in-vivo image that is main-displayed may be a moving image or a still image.

As illustrated in FIG. 4, when the slider 106 designated by a distal end of a pointer 109 is moved by performing an operation of moving the pointer 109 on the screen with a mouse, a touch panel, or the like, images displayed in the main display area 103 are switched to in-vivo images 103c and 103d that correspond to the image captured time designated by the slider 106. In addition, in accordance with the movement of the slider 106, the label extracting unit 18 extracts, from the label storing unit 14c, lesion labels according to an organ that corresponds to the area designated by the slider 106. Furthermore, the display control unit 19 causes the display unit 15 to display icons that correspond to the extracted lesion labels within the label box display area 108. For example, FIG. 4 illustrates a state in which the slider 106 designates an area 107c that corresponds to the small intestine. At this time, in the label box display area 108, an icon 112a representing hemorrhage, an icon 112b representing angiodysplasia, and an icon 112c representing tumor are displayed in correspondence with the small intestine.

In the image observation screen 100, if a pointer operation of associating one of the reduced images 105a, 105b, . . . displayed in the thumbnail area 105, with one of the icons 112a to 112c is performed, the label assigning unit 20 assigns, to the in-vivo image, a lesion label corresponding to an icon associated with an in-vivo image that corresponds to the reduced image selected by the pointer.

For example, if a user determines that angiodysplasia is recognizable by visual observation in the reduced image 105d, the user drags the reduced image 105d and drops it on the icon 112b that represents angiodysplasia (a broken-lined arrow illustrated in FIG. 4). Accordingly, the label assigning unit 20 assigns an angiodysplasia label to the in-vivo image that corresponds to the reduced image 105d and stores it in the image data storing unit 14a in association with the image data.

The operation of associating a reduced image and an icon with each other is not limited to the above-described drag-and-drop, and for example, it may be an operation of dragging an icon and dropping it on a reduced image, an operation of clicking an icon in a state in which a reduced image is selected, or the like.

Thereafter, the display control unit 19 causes the display unit 15 to display, near the reduced image, textual information that corresponds to the lesion label assigned to the in-vivo image. For example, in the image observation screen 100 illustrated in FIG. 5, textual information "angiodysplasia" that corresponds to the angiodysplasia label is displayed in a label display area 110 that is located below the reduced image 105d.

As described above, according to the first embodiment, since the icons that correspond to the additional information that is extracted in accordance with the feature quantity of an image are displayed on the screen, a user is able to assign the additional information to the image simply and efficiently by only performing the operation of associating the desired image and the icon with each other on the screen. In other words, the user is able to assign lesion labels to desired in-vivo images by performing only a simple operation of selecting the reduced images 105a, 105b, . . . and dragging and dropping them to the icons located within the label box display area 108. In addition, since only the icons that correspond to the organ that is designated by the slider 106 are displayed in the label box display area 108, the user is able to select a desired icon easily. Accordingly, it is possible to reduce significantly burden on the user in a label assigning operation.

Furthermore, according to the first embodiment, since each in-vivo image is managed by assigning a lesion label thereto, for example, it is possible to easily extract, at a later stage (for example, at a stage of creating a report), an in-vivo image that has been taken note of during image observation.

Modified Example 1-1

Figure 6:
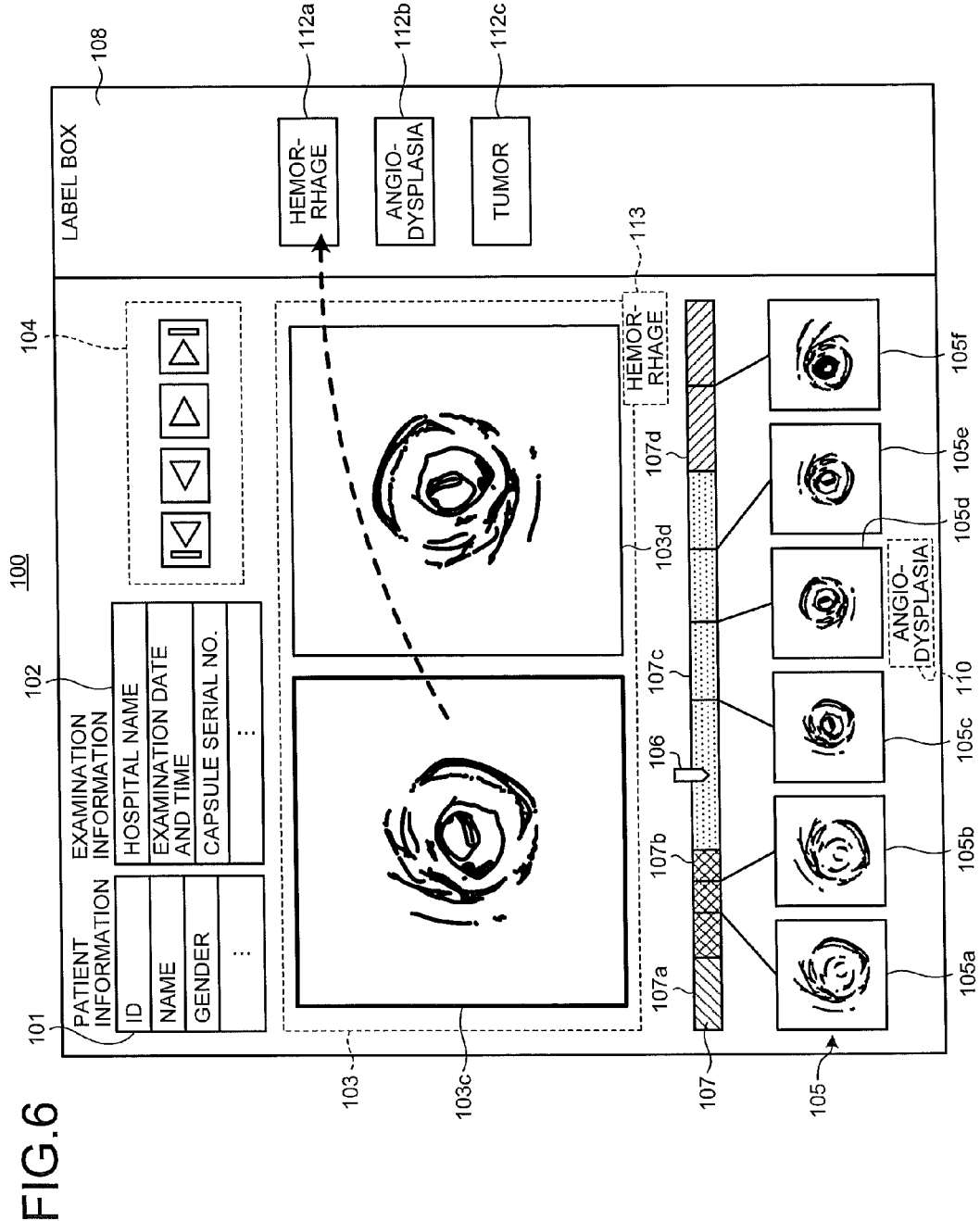
FIG. 6 is a schematic diagram that illustrates a display example of an image observation screen according to Modified Example 1-1.

The above-described label assigning operation may be performed by an operation of associating an in-vivo image displayed in the main display area 103 with a desired icon. More specifically, as illustrated in FIG. 6, an operation of drag-and-drop or the like of the in-vivo image 103c or 103d, which is main-displayed, with respect to a desired icon in the label box display area 108 is performed. FIG. 6 illustrates the in-vivo image 103c being dragged and dropped with respect to an icon 112a that represents hemorrhage, and, in this case, the label assigning unit 20 assigns the hemorrhage label to the in-vivo image 103c. At this time, the display control unit 19 may display, near the in-vivo image 103c or 103d, textual information that corresponds to the assigned lesion label. For example, in FIG. 6, textual information "hemorrhage" that corresponds to the hemorrhage label is displayed in a label display area 113 located below the in-vivo image 103d. Alternatively, the display control unit 19 may display, in the thumbnail area 105, a reduced image of the in-vivo image to which the lesion label has been assigned, and display, in a label display area 110 near the reduced image, textual information that corresponds to the assigned lesion label.

Modified Example 1-2

Figure 7:
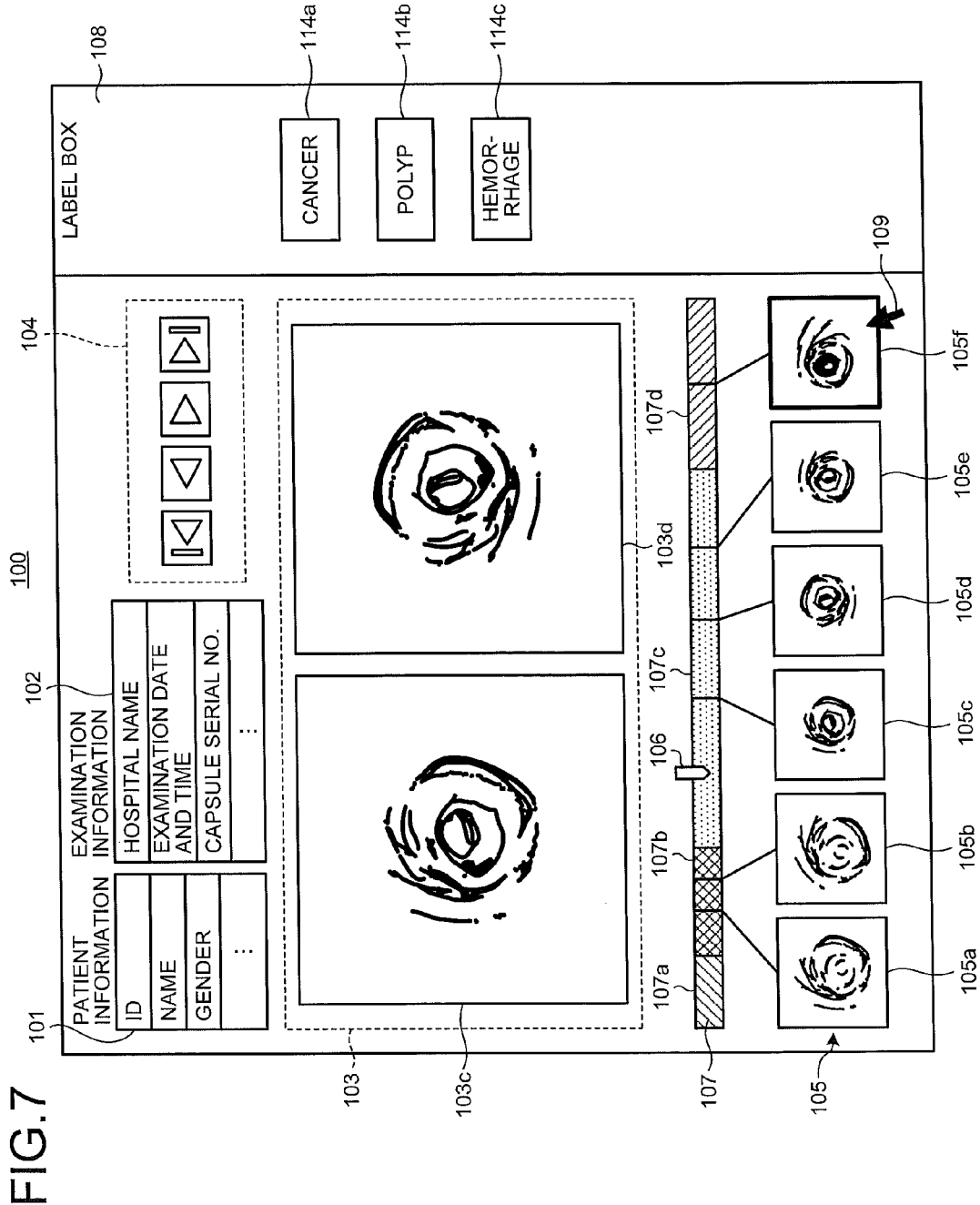
FIG. 7 is a schematic diagram that illustrates a display example of an image observation screen according to Modified Example 1-2.

The icons that are displayed within the label box display area 108 may be set in accordance with an image that is selected by a user. For example, as illustrated in FIG. 7, when a reduced image 105f is selected by performing a pointer operation on the screen, the label extracting unit 18 extracts corresponding lesion labels based on a color feature quantity of the in-vivo image that corresponds to the reduced image 105f (or in accordance with an organ label if the organ label is assigned in advance). In addition, the display control unit 19 causes the display unit 15 to display icons that correspond to the extracted lesion labels. FIG. 7 illustrates a state in which an icon 114a representing cancer, an icon 114b representing polyp, and an icon 114c representing hemorrhage are displayed in the label box display area 108 in correspondence with the reduced image 105f that represents large intestine.

Modified Example 1-3

Figure 8:
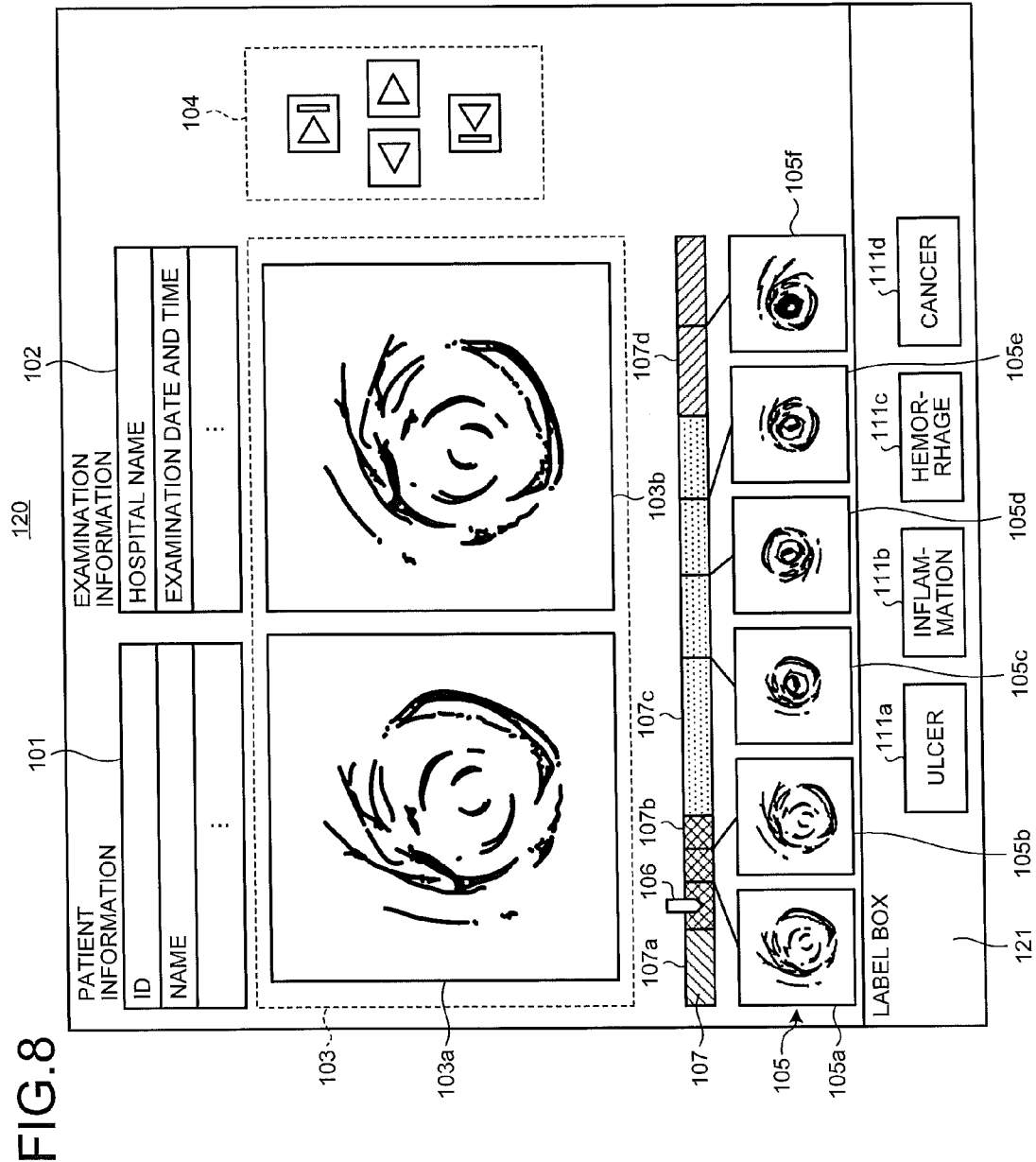
FIG. 8 is a schematic diagram that illustrates a display example of an image observation screen according to Modified Example 1-3.

The label box display area may be arranged at any position within the screen. More specifically, the label box display area may be arranged at any position closer to an upper side, a lower side, a right side, or a left side on the screen and may be arranged in any one of a horizontal direction and a vertical direction. For example, FIG. 8 illustrates an example in which a label box display area 121 is arranged along the lower side of an image observation screen 120. In this case, since a distance from the icons 111a to 111d in the label box display area 121 to the reduced images 105a, 105b, . . . in the thumbnail area 105 becomes smaller, an amount of movement in the drag-and-drop decreases, and burden on the user in a label assigning operation is able to be further reduced.

Modified Example 1-4

Figure 9:
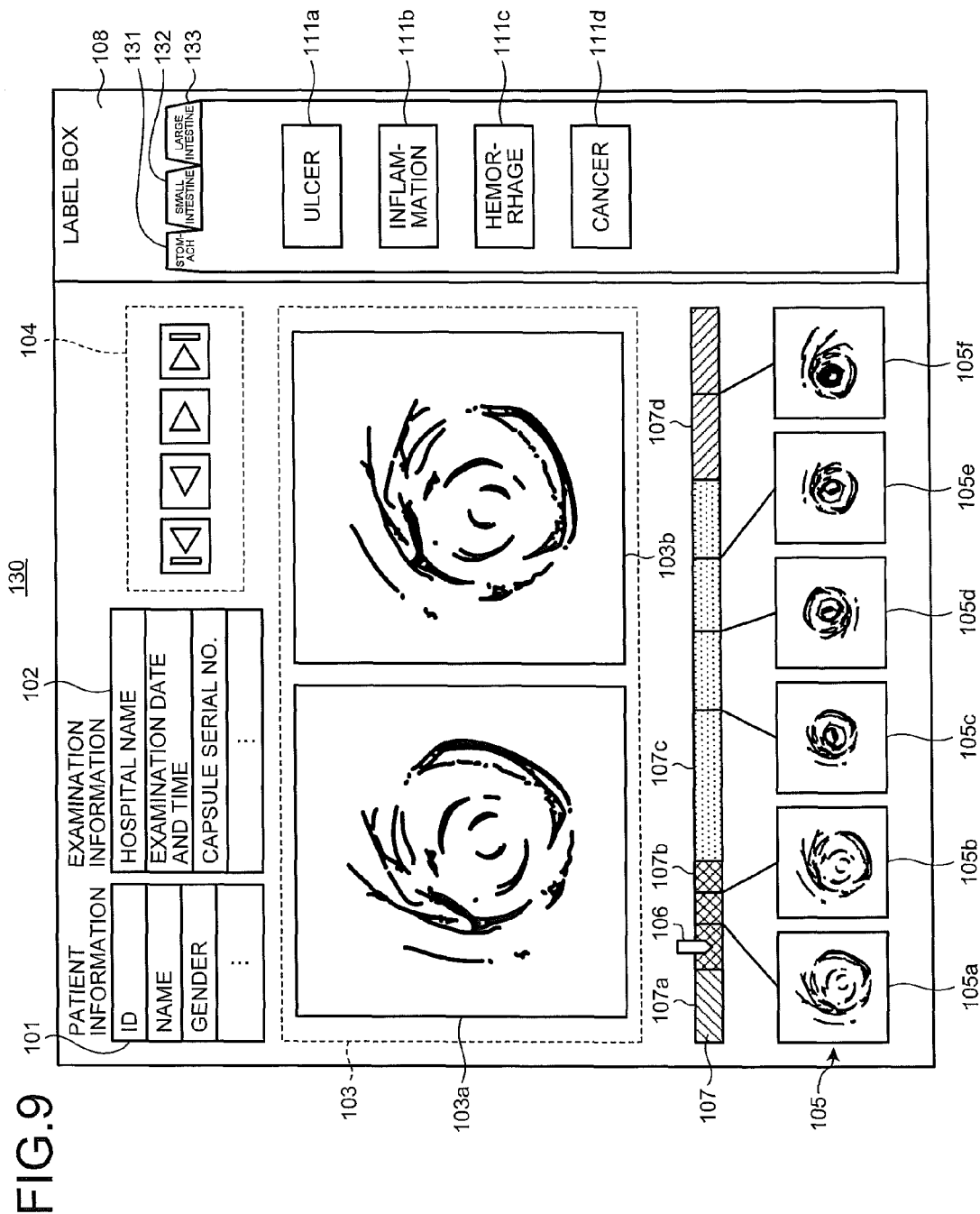
FIG. 9 is a schematic diagram that illustrates a display example of an image observation screen according to Modified Example 1-4.

The icons displayed within the label box display area may be changed in accordance with a user's selection. For example, as illustrated in FIG. 9, a plurality of tab screens 131 to 133 that are classified by organ are provided within the label box display area 108 of an image observation screen 130, and icons that correspond to the lesion labels for each organ are displayed on the respective tab screens 131 to 133. FIG. 9 illustrates a state in which the tab screen 131 that corresponds to stomach is selected and displayed at the forefront. A user is able to cause a desired tab screen to be displayed at the forefront by selecting the tab screen through a pointer operation on the image observation screen 130. Alternatively, the tab screen that is displayed at the foremost may be switched in association with an organ designated by an operation with respect to the slider 106 on the time bar 107.

Modified Example 1-5

A display format or an arrangement of the icons within the label box display area is not particularly limited.

As for a display format of an individual icon, a corresponding lesion name may be displayed on each icon as text (for example, see icons 111a to 111d illustrated in FIG. 3), or a mark that represents a corresponding lesion name may be displayed on each icon. In addition, the text or the mark displayed on each icon may be editable or changeable in accordance with a user's taste. If a lesion name displayed on an icon is to be edited, dictionary data (terminology data that is used in creating a report or the like) that is built in the image management apparatus 5 may be linked thereto. Thereby, the operation for a user in creating a report is able to be simplified.

In addition, the kinds of icons displayed for each organ within the label box display area may be set by default, or may be added, removed, edited (change in label name), or the like in accordance with a user's preference.

As for the arrangement of icons within the label box display area, for example, the lesion names may be set in order of Japanese syllabary or in alphabetic order or may be set in accordance with frequencies of use of the icons (in other words, frequency at which the lesion label is assigned). If the arrangement is set in accordance with the frequencies of use of the icons, the arrangement may be set based on occurrence frequencies of lesions that are statistically obtained, or the number of times for which each lesion label has been assigned to an in-vivo image in the image management apparatus 5 may be counted and the arrangement may be set in accordance with the number of times thereof.

When the arrangement of icons is determined in accordance with the frequencies of use of the icons, an icon having a high frequency of use may be arranged near the thumbnail area. For example, as illustrated in FIG. 3, if the label box display area 108 is arranged along the right side of the image observation screen 100, an icon having a high frequency of use is arranged at a lower end of the screen. Accordingly, the amount of movement of the pointer upon performing the drag-and-drop of the reduced images 105a, 105b, . . . onto the icons 111a to 111d decreases, and thus burden on a user in a label assigning operation is able to be reduced.

Modified Example 1-6

Figure 10:
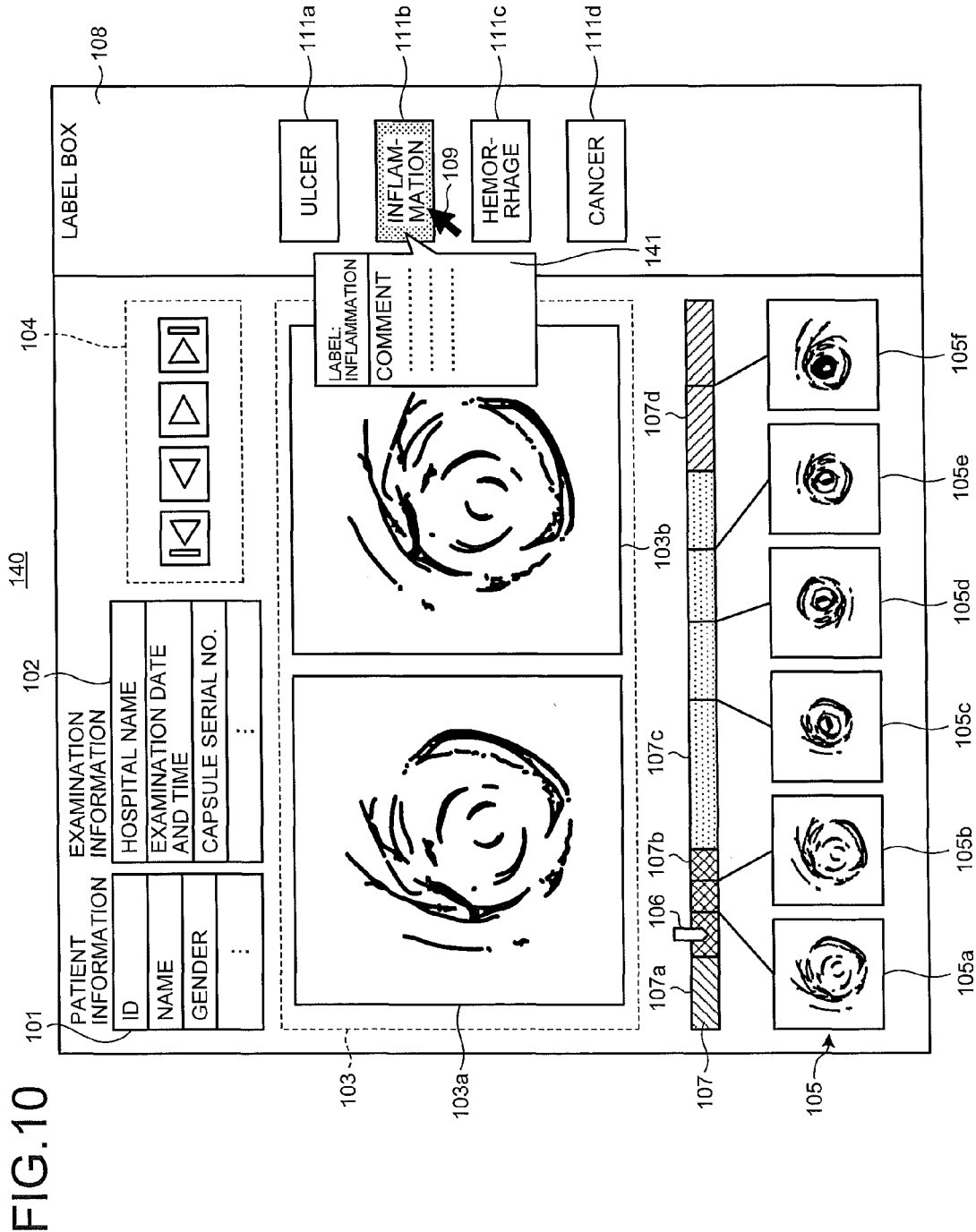
FIG. 10 is a schematic diagram that illustrates a display example of an image observation screen according to Modified Example 1-6.

By performing an operation of associating the image (the reduced image or the image that is mainly displayed) displayed on the screen with an icon in the label box display area, various kinds of information other than a lesion label may be assigned to an in-vivo image. FIG. 10 is a display example of an image observation screen on which comments are able to be added to the in-vivo images. In an image observation screen 140 illustrated in FIG. 10, when a predetermined pointer operation (for example, a right-click of a mouse) is performed with respect to an icon that is intended by a user, the display control unit 19 causes the display unit 15 to display a comment input window 141 provided with a text input field. The control unit 16 stores, in the label storing unit 14c, text information that is input in accordance with a text input operation with respect to the comment input window 141, in association with a lesion label that corresponds to the selected icon. FIG. 10 illustrates a state in which the comment input window 141 is displayed with respect to the icon 111b that represents inflammation.

As described, if an in-vivo image is associated with an icon for which a comment has been input through a pointer operation on the screen, the label assigning unit 20 assigns the lesion label and adds the comment to the in-vivo image and stores them in the storage unit 14 in association with the image data. Accordingly, for example, when a report is created, the comment is in a state of already having been input, and thus the user is able to save the labor of inputting the comment. In addition, even if a medical doctor differs from a report creator, medical judgment by the medical doctor is able to be correctly conveyed to the report creator through the added comment.

Modified Example 1-7

Figure 11:
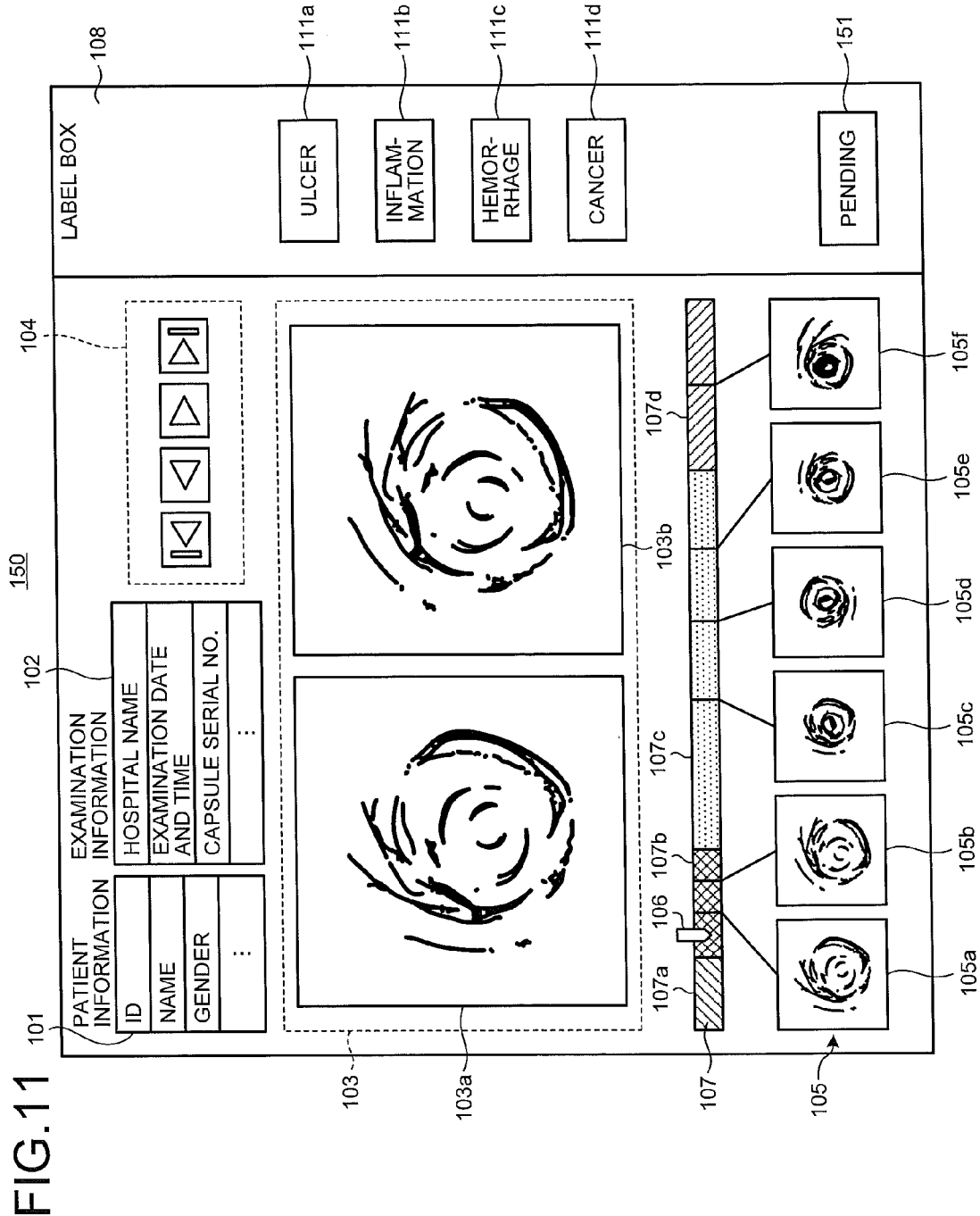
FIG. 11 is a schematic diagram that illustrates a display example of an image observation screen according to Modified Example 1-7.

When a user recognizes concerning findings in an in-vivo image that is being observed but is unable to determine what a lesion is, the user may wish to manage such an in-vivo image distinctively from other in-vivo images. Thus, a label (for example, a pending label) to be temporarily assigned to an in-vivo image for which a judgment has been pending may be provided. An image observation screen 150 illustrated in FIG. 11 illustrates an example in which an icon 151 corresponding to a pending label is displayed in the label box display area 108. By providing such an icon, the user is able to later extract and observe in detail the in-vivo images to which the pending label have been assigned, and determine the user's judgment. Accordingly, the user is able to smoothly promote observation of a series of in-vivo images and improve operation efficiency.

Modified Example 1-8

Figure 12:
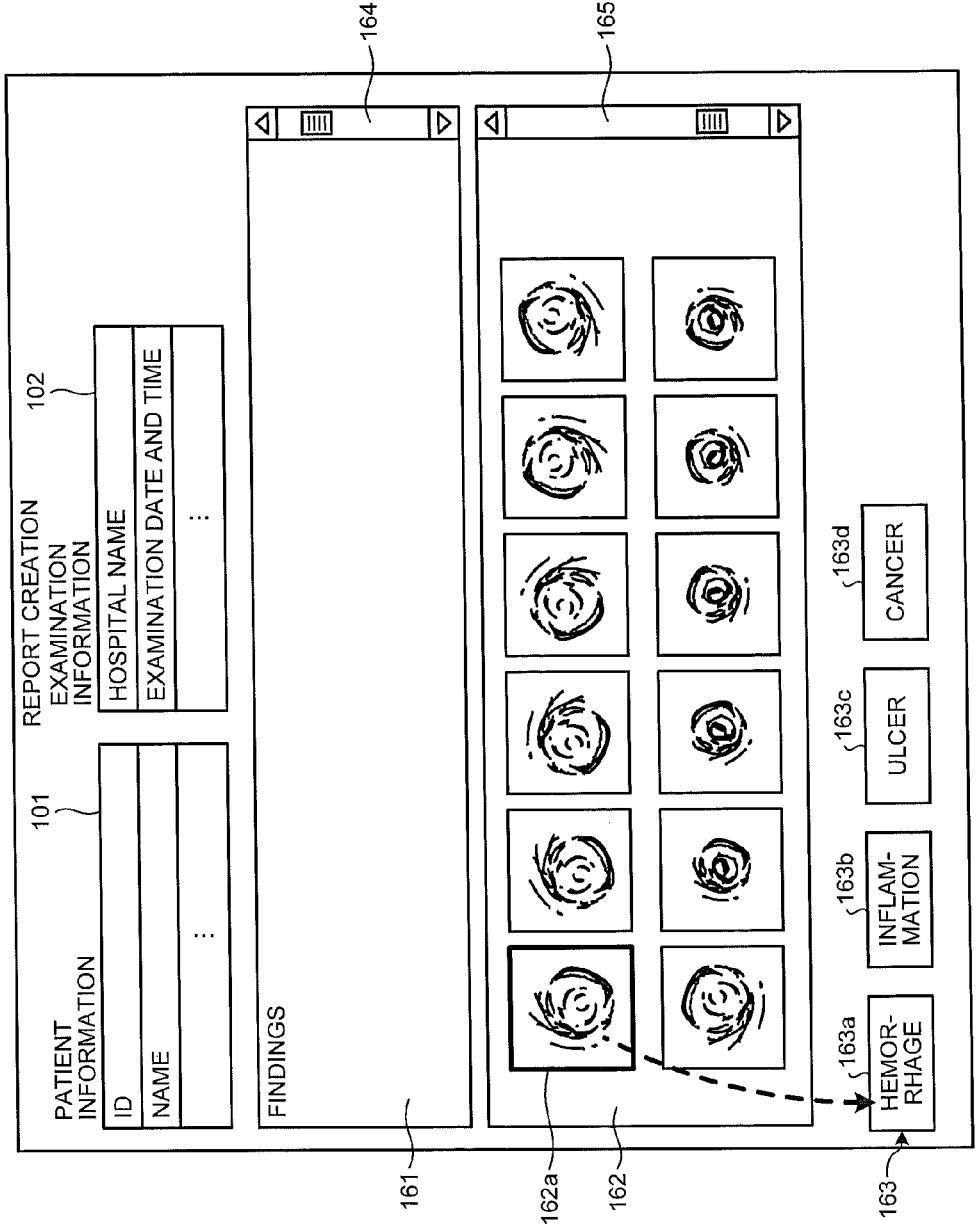
FIG. 12 is a schematic diagram that illustrates a display example of a report creation screen according to Modified Example 1-8.

The label assigning operation using an icon that corresponds to a lesion label may be performed on a screen other than the image observation screen. FIG. 12 is a display example of a case in which such a label assigning operation is performed on a report creation screen.

A report creation screen 160 illustrated in FIG. 12 includes: a findings input area 161 for entering a user's findings; a captured image display area 162 in which a captured image selected by the user during the observation process is displayed on a reduced scale; and a label box display area 163 in which icons 163a to 163d corresponding to a lesion label are arranged, in addition to the patient information area 101 and the examination information area 102. Of these, the findings input area 161 and the captured image display area 162 are provided with scroll bars 164 and 165.

When any of captured images is selected through a pointer operation on the report creation screen 160, the label extracting unit 18 extracts a lesion label that corresponds to the selected captured image. Accordingly, the display control unit 19 causes the display unit 15 to display, in the label box display area 163, icons that correspond to the extracted lesion label. For example, in FIG. 12, in correspondence with a captured image 162a that represents stomach, an icon 163a that represents hemorrhage, an icon 163b that represents inflammation, an icon 163c that represents ulcer, and an icon 163d that represents cancer, which are lesion labels corresponding to stomach, are displayed in the label box display area 163.

Further, when the selected captured image and one of the icons 163a to 163d are associated with each other through a pointer operation on the screen, the label assigning unit 20 assigns the lesion label that corresponds to the icon to an in-vivo image that corresponds to the selected captured image. For example, FIG. 12 illustrates the manner of dragging the captured image 162a and dropping it onto the icon 163a.

As described, on the report creation screen 160 also, a user is able to assign lesion labels to in-vivo images by a simple operation. Accordingly, at a stage of creating a report, an operation of looking at the image observation screen again for assigning lesion labels to in-vivo images is not necessary, and thus operation efficiency is able to be improved.

Modified Example 1-9

The number of lesion labels that are able to be assigned to one in-vivo image is not limited. For example, if two or more lesion labels are desired to be assigned to an in-vivo image, the operation of dragging the in-vivo image (or a reduced image in the thumbnail area) displayed on the screen and dropping it to desired icons may be sequentially performed. Accordingly, the lesion labels that correspond to the icons onto which the in-vivo image has been dropped are sequentially added and assigned to the in-vivo image.

Further, a lesion label that has been assigned to an in-vivo image may be deletable. For example, by a predetermined pointer operation (for example, a right-click of a mouse) with respect to a desired in-vivo image (or a reduced image in the thumbnail area), a delete menu for lesion labels may be displayed, and, the lesion label that has been assigned to the in-vivo image may be deleted in accordance with a pointer operation with respect to the delete menu. Alternatively, a delete icon for deleting a lesion label may be provided on the screen, and a lesion label may be deleted from an in-vivo image through a pointer operation of dragging the in-vivo image to which the lesion label has been assigned and dropping it onto the delete icon.

Furthermore, the lesion label that has been assigned to the in-vivo image may be changeable. In that case, the lesion label may be deleted as described above, and a pointer operation (drag-and-drop onto an icon that corresponds to a desired lesion label) of newly assigning a lesion label may be performed. Alternatively, by performing a pointer operation of associating the in-vivo image to which the lesion label has been already assigned with an icon that corresponds to another lesion label, the lesion label of the in-vivo image may be changed to the another lesion label. In that case, operations may be set such that the pointer operation for adding the lesion label and the pointer operation for changing the lesion label are different from each other. For example, if the lesion label is added, the in-vivo image may be dragged with a left button of the mouse being pressed and dropped onto an icon that corresponds to a desired lesion label. If the lesion label is changed, the in-vivo image may be dragged with a right button of the mouse being pressed and dropped onto an icon that corresponds to the desired lesion label.

Second Embodiment

Next, a second embodiment of the present invention will be described.

Figure 13:
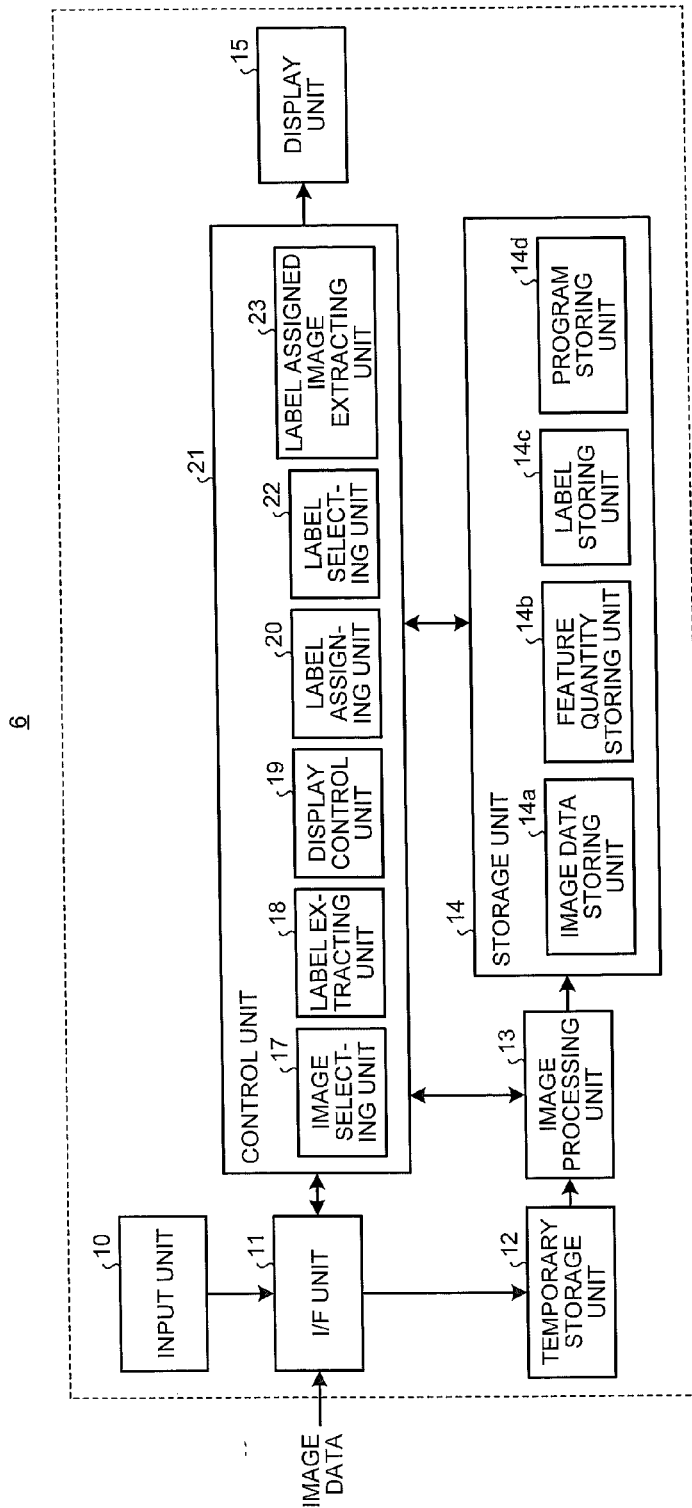
FIG. 13 is a block diagram that illustrates a configuration of an image management apparatus according to a second embodiment of the invention.

FIG. 13 is a block diagram that illustrates a configuration of an image management apparatus according to the second embodiment. As illustrated in FIG. 13, an image management apparatus 6 according to the second embodiment includes a control unit 21, in the configuration of the control unit 16 illustrated in FIG. 2, added with a label selecting unit 22 and a label assigned image extracting unit 23. The label selecting unit 22 selects a lesion label that corresponds to an icon that is selected by a pointer operation on the screen. The label assigned image extracting unit 23 extracts in-vivo images to which the lesion label selected by the label selecting unit 22 has been assigned. The rest of the configuration is similar to that illustrated in FIG. 2.

Figure 14:
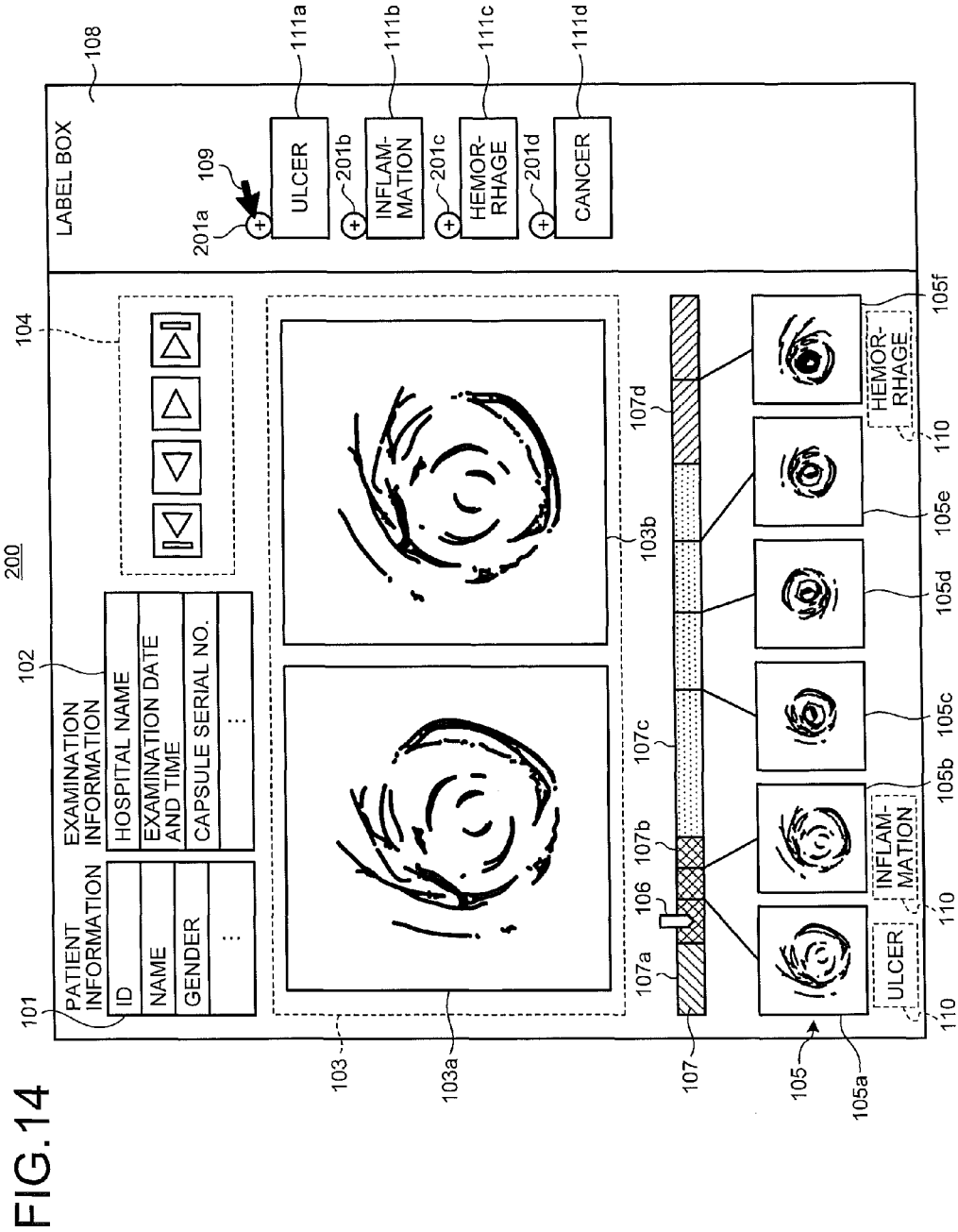
FIG. 14 is a schematic diagram that illustrates a display example of an image observation screen according to the second embodiment.
Figure 15:
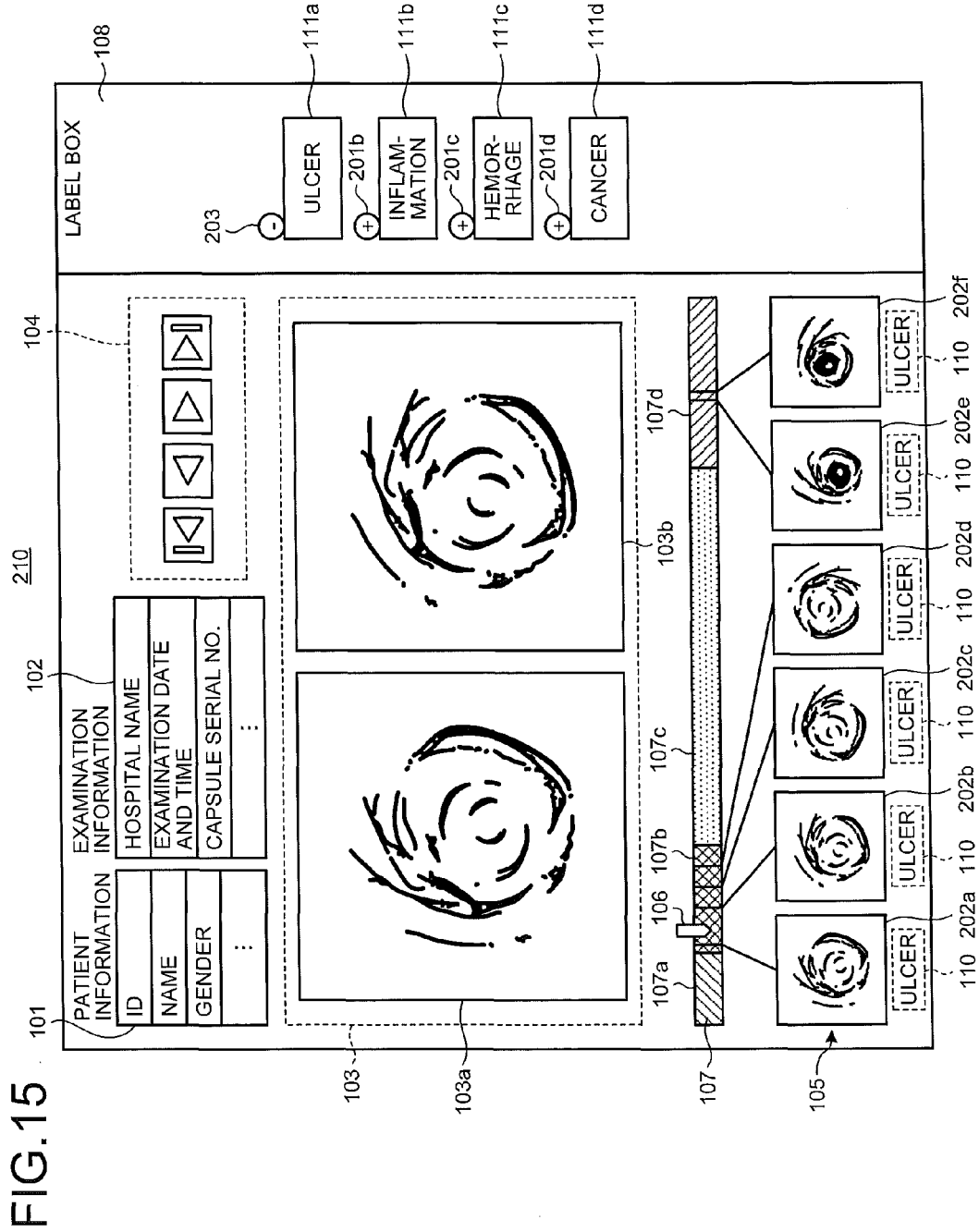
FIG. 15 is a schematic diagram that illustrates a display example of an image observation screen according to the second embodiment.
Figure 16:
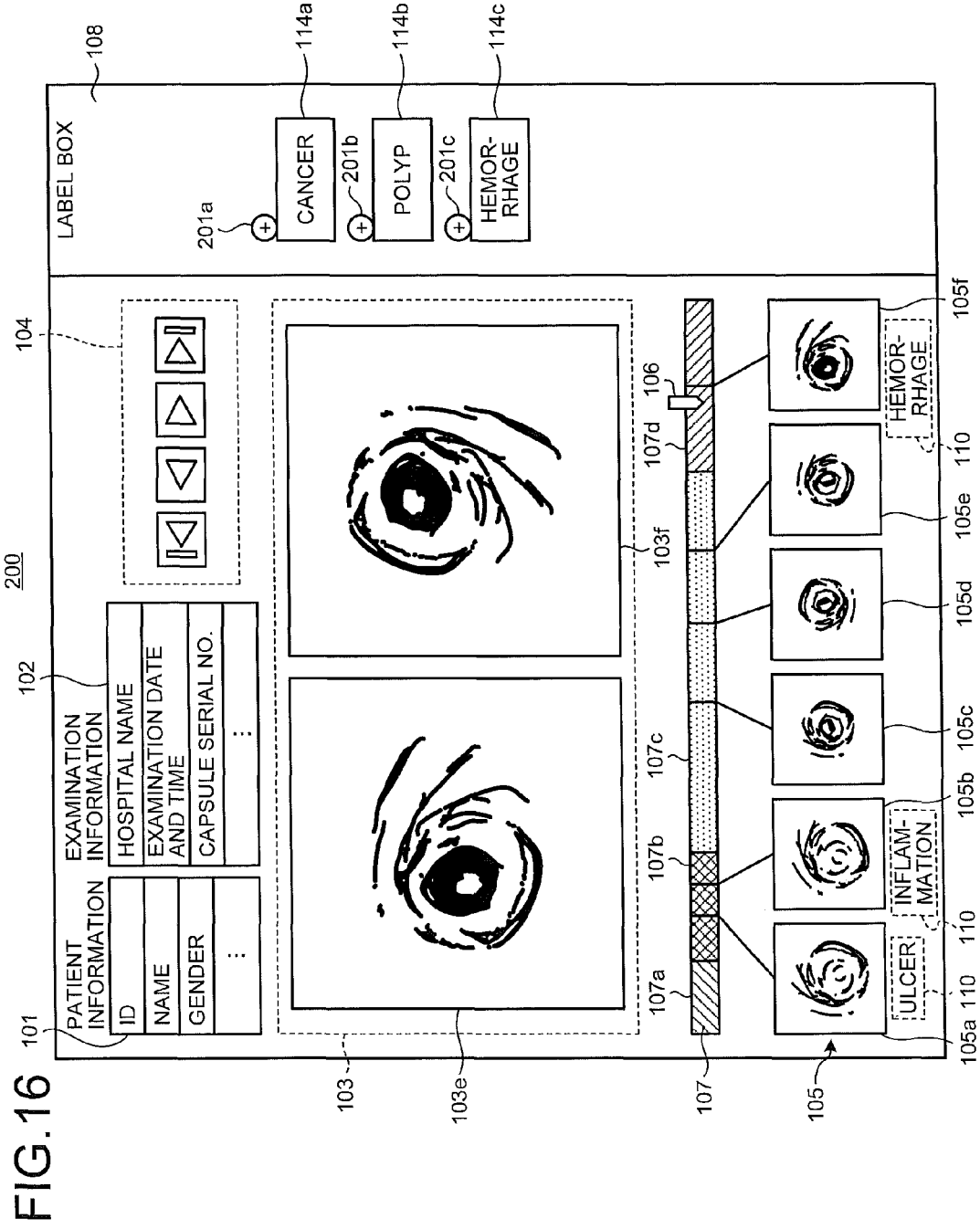
FIG. 16 is a schematic diagram that illustrates a display example of an image observation screen according to the second embodiment.

Next, operation of the image management apparatus 6 will be described with reference to FIGS. 14 to 16. FIGS. 14 to 16 are schematic diagrams that illustrate display examples of an image observation screen that is displayed on the display unit 15.

On an image observation screen 200 illustrated in FIG. 14, expansion buttons 201a to 201d are respectively displayed near icons 111a to 111d in a label box display area 108. In addition, in the label display areas 110 near the reduced images 105a, 105b, and 105f to which labels have been assigned, of the reduced images 105a, 105b, . . . in the thumbnail area 105, lesion labels assigned respectively thereto are displayed.

If any of the expansion buttons 201a to 201d is selected by a pointer operation on the image observation screen 200, the label assigned image extracting unit 23 extracts, from the in-vivo images that are stored in the storage unit 14, in-vivo images to which a lesion label of an icon that corresponds to the selected expansion button has been assigned. In addition, the display control unit 19 causes the display unit 15 to display reduced images of the in-vivo images extracted by the label assigned image extracting unit 23 in a thumbnail area 105. An image observation screen 210 illustrated in FIG. 15 illustrates an example in which reduced images 202a to 202f of the in-vivo images to which an ulcer label has been assigned are displayed expanded in the thumbnail area 105 as a result of the expansion button 201a that corresponds to the icon 111a representing ulcer being selected. At this time, the expansion button 201a (see FIG. 14) that is displayed near the icon 111a is changed to a fold button 203.

If the fold button 203 is selected by a pointer operation on the image observation screen 210, the display control unit 19 switches the display in the thumbnail area 105 to the original reduced images (a display of reduced images 105a, 105b, . . . , which are selected by a user) (see FIG. 14).

If any of the reduced images 202a to 202f is selected by a predetermined pointer operation (for example, a click on a desired reduced image) on the image observation screen 210, the display control unit 19 causes an in-vivo image that corresponds to the selected reduced image and its adjacent image (in-vivo images of adjacent image captured times) to be displayed in the main display area 103 and switches the display in the thumbnail area 105 to ordinary reduced images according to the user's selection. For example, if the reduced image 202*f* is selected in FIG. 15, an in-vivo image 103*e* that corresponds to the reduced image 202*f* and an in-vivo image 103*f* that is captured subsequently thereto are displayed in the main display area 103 (FIG. 16). At this time, with transition of the images in the main display area 103 (in other words, the movement of the slider 106), icons 114*a* to 114*c* displayed in the label box display area 108 change too.

As described above, according to the second embodiment, since the in-vivo-images to which a lesion label that is desired by a user has been assigned is able to be extracted and displayed by only an operation of selecting an icon that corresponds to the lesion label, convenience for the user performing an image observation operation is able to be improved.

Further, according to the second embodiment, since the in-vivo images are able to be managed by being grouped per lesion label, a user is able to use the group of in-vivo images to which a desired lesion label has been assigned by a simple operation.

Modified Example 2-1

By using icons that correspond to lesion labels, various processes are able to be performed for a group of in-vivo images for each lesion label.

Figure 17:
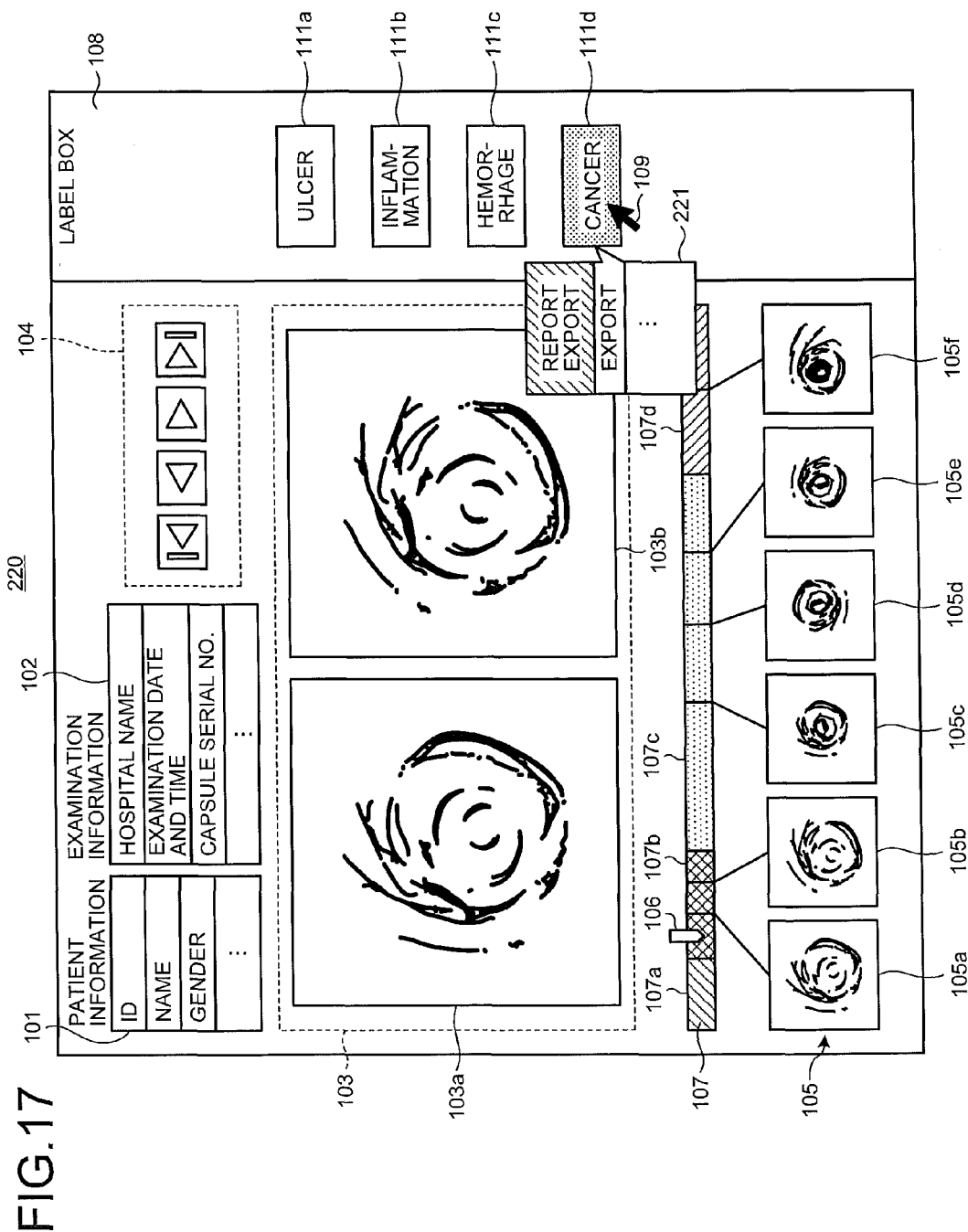
FIG. 17 is a schematic diagram that illustrates a display example of an image observation screen according to Modified Example 2-1.

FIG. 17 illustrates a case in which a group of in-vivo images for each lesion label are output at once. On an image observation screen 220 illustrated in FIG. 17, if a predetermined pointer operation (for example, a double click, a right click, or the like on an icon) is performed with respect to an icon desired by a user, the display control unit 19 causes the display unit 15 to display a menu in which commands related to processing of the in-vivo image are written near the icon. For example, FIG. 17 illustrates a state in which a menu 221, in which an output process (export) by attachment of an in-vivo image to a report file and an output process of an in-vivo image to an external device are written, is displayed with respect to the icon 111*d* that represents cancer.

If a process desired by a user is selected by a pointer operation with respect to the menu 221, the label assigned image extracting unit 23 extracts a group of in-vivo images to which a lesion label corresponding to the icon (in the case of FIG. 17, an icon 111*d*) has been assigned, and the control unit 21 collectively performs the process selected with respect to the extracted group of in-vivo images. For example, in the case of FIG. 17, a group of in-vivo images to which the cancer label has been assigned are output by attachment to a report file.

Modified Example 2-2

Figure 18:
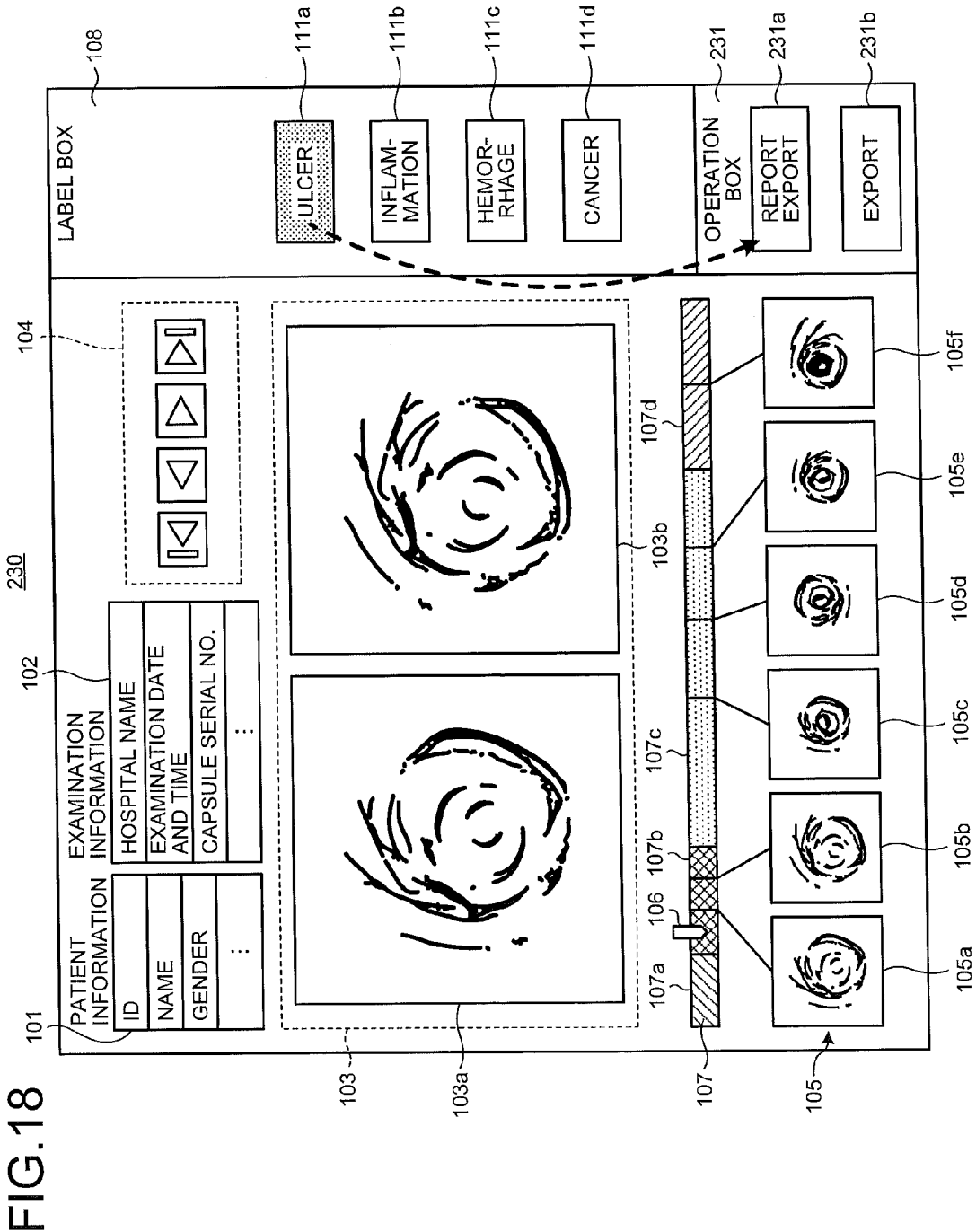
FIG. 18 is a schematic diagram that illustrates a display example of an image observation screen according to Modified Example 2-2.

If a group of in-vivo images for each lesion label are processed at once, icons that correspond to processes with respect to the group of in-vivo images may be displayed on the screen. For example, on an image observation screen 230 illustrated in FIG. 18, an operation box display area 231 is provided in which an icon 231*a* that represents a report export process and an icon 231*b* that represents an export process are displayed. In such an image observation screen 230, when a pointer operation of associating an icon that corresponds to a lesion label desired by a user with an icon corresponding to a process desired by the user is performed, the control unit 21 performs a process corresponding to the selected icon with respect to the group of in-vivo images to which the lesion label desired by the user has been assigned. For example, FIG. 18 illustrates a state in which an icon 111*a* representing ulcer is dragged and dropped to the icon 231*a*. In this case, the group of in-vivo images to which the ulcer label has been assigned are attached together to a report file.

Modified Example 2-3

Figure 19:
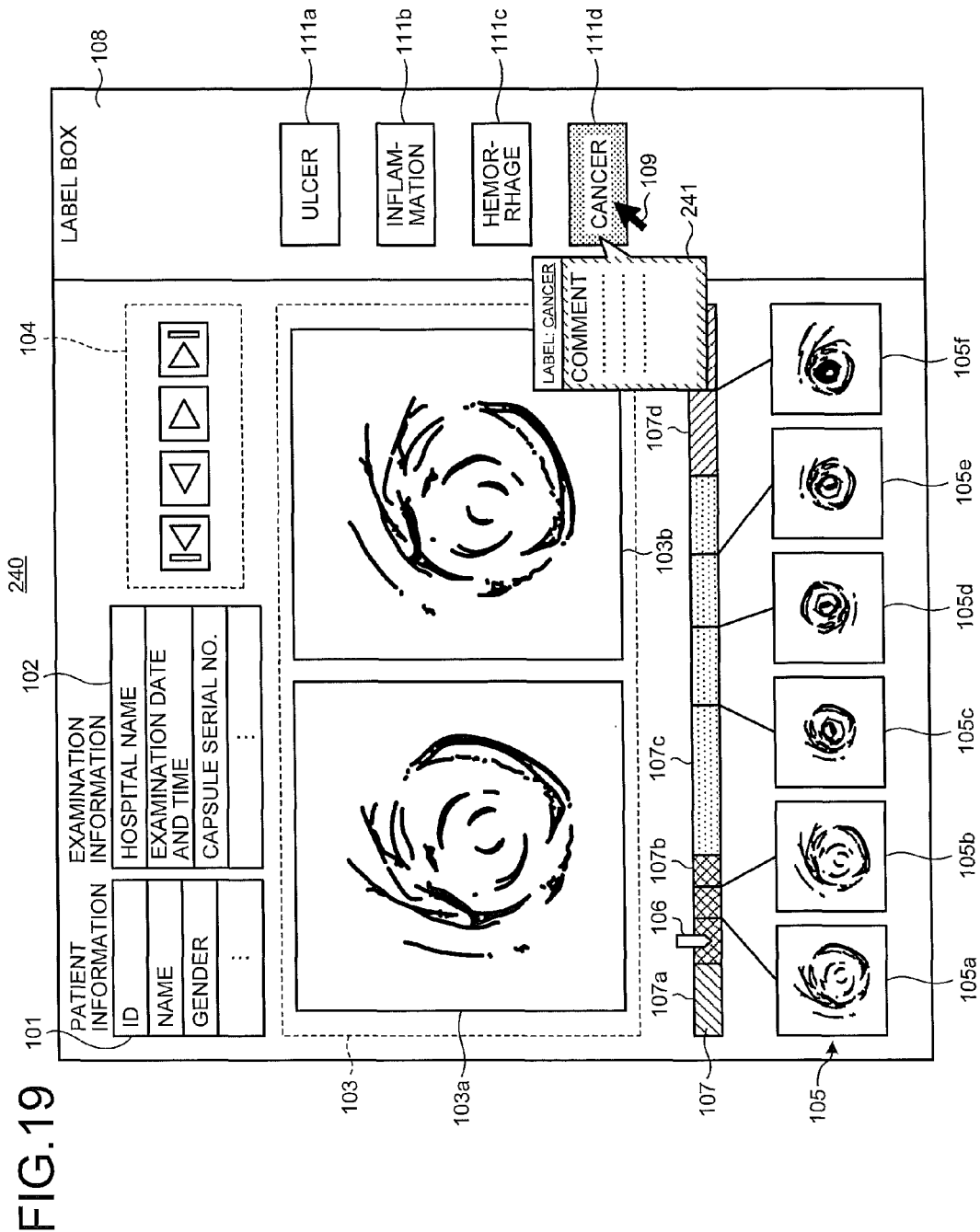
FIG. 19 is a schematic diagram that illustrates a display example of an image observation screen according to Modified Example 2-3.

FIG. 19 is a display example of a screen on which additional information is collectively edited with respect to a group of in-vivo images for each lesion label. On an image observation screen 240 illustrated in FIG. 19, if a predetermined pointer operation (for example, a double click or a right click using a mouse) is performed for an icon that corresponds to a lesion label desired by the user, the display control unit 19 causes the display unit 15 to display a text input window near the icon. For example, FIG. 19 illustrates a state in which a label editing window 241, in which a text input field for editing a lesion name and a text input field for inputting a comment are provided, is displayed near an icon 111*d* that represents cancer.

If a text input operation is performed with respect to the label editing window 241, the control unit 21 collectively performs processes of changing/modifying a lesion name, adding comments, or the like, with respect to in-vivo images to which the lesion label corresponding to the selected icon has been assigned. For example, in the case of FIG. 19, comments are added collectively with respect to the in-vivo images to which the cancer label has been assigned. In this way, even if there is a clerical error or the like in a lesion name of a lesion label or a comment, there is no need to modify for every in-vivo image, and collective modification becomes possible.

Modified Example 2-4

Figure 20:
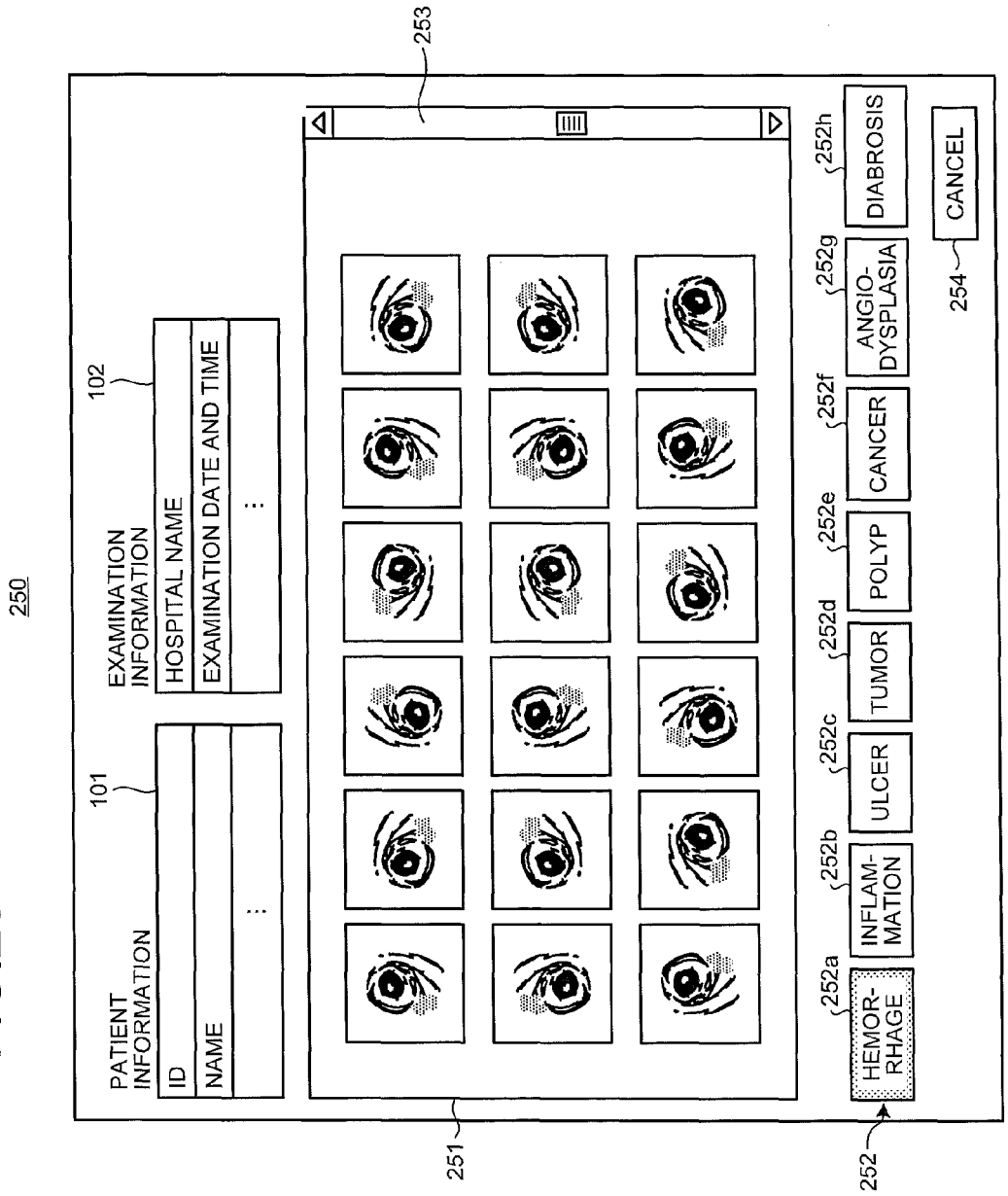
FIG. 20 is a schematic diagram that illustrates a display example of an overview (still image list display) screen according to Modified Example 2-4.

FIG. 20 is a display example of a case in which a collective process with respect to a group of in-vivo images for each lesion label is performed on an overview (still image list display) screen. Images to be displayed on an overview screen 250 are all of the in-vivo images or in-vivo images (representative images) that are extracted based on a predetermined extraction condition or an extraction condition that is set by a user.

The overview screen 250 illustrated in FIG. 20 includes: a patient information area 101 in which identification information of a subject 1 that is a patient is displayed; an examination information area 102 in which identification information of an examination that is performed with respect to the subject 1 is displayed; a list display area 251 in which a list of still images of in-vivo images are displayed; and a label box display area 252 in which icons 252*a* to 252*h* that correspond to lesion labels are displayed. Of these, in the list display area 251, a scroll bar 253 is provided. In addition, a cancel button 254 that is used in canceling selection with respect to the icons 252*a* to 252*h* is also displayed in the label box display area 252.

On the overview screen 250, if none of the icons 252*a* to 252*h* is selected, the display control unit 19 causes the display unit 15 to display all of the in-vivo images in predetermined order (for example, the order of image captured time) and in a predetermined arrangement (for example, in order from left to right) in the list display area 251 based on the image data stored in the storage unit 14.

If any of the icons 252*a* to 252*h* is selected by a pointer operation performed on the screen, the label assigned image extracting unit 23 extracts from the storage unit 14 in-vivo images to which a lesion label corresponding to the selected icon has been assigned. In addition, the display control unit 19 causes the display unit 15 to display the extracted in-vivo images in the predetermined order and the predetermined arrangement described above in the list display area 251. For example, FIG. 20 illustrates a state in which the icon 252a representing hemorrhage is selected, and a group of in-vivo images to which the hemorrhage label has been assigned are displayed.

In addition, if, in a state in which one of the icons 252a to 252h is selected by a pointer operation on a screen, another icon is further selected, the label assigned image extracting unit 23 further extracts in-vivo images which correspond to the newly-selected icon. In addition, the display control unit 19 causes the display unit 15 to display the newly extracted in-vivo images in addition to the in-vivo images that are already displayed in the list display area 251. For example, in the case of FIG. 20, if the icon 252c representing ulcer is selected after the icon 252a representing hemorrhage, a group of in-vivo images to which the ulcer label has been assigned are displayed in the list display area 251 subsequently to the group of the in-vivo images to which the hemorrhage label has been assigned.

Furthermore, when a predetermined pointer operation (for example, a click) is performed with respect to the cancel button 254, the selection with respect to the icons 252a to 252h is canceled. In this case, the display control unit 19 causes the display unit 15 to display all of the in-vivo images that are display targets of the overview screen 250 again in the list display area 251.

As described above, according to Modified Example 2-4, the in-vivo images are able to be displayed per lesion label as a list.

Modified Example 2-5

In Modified Example 2-4, although only a group of in-vivo images to which a lesion label desired by the user has been assigned are displayed on the screen as a list, all of the in-vivo images may be displayed per lesion label, which have been changed in order as desired by the user. In this case, for example, all the icons 252a to 252h illustrated in FIG. 20 may be selected in the order desired by the user.

Modified Example 2-6

The overview screen as illustrated in FIG. 20 may be directly transitable from a normal image observation screen. For example, on the image observation screen 100 illustrated in FIG. 3, if any of the icons 111a to 111d in the label box display area 108 is selected by a predetermined point operation (for example, a double click), the display control unit 19 causes the display unit 15 to display an overview screen 250 on which a group of in-vivo images to which a lesion label corresponding to the operated icon has been assigned are displayed as a list. On the contrary, on the overview screen 250, if any of the in-vivo images in the list display area 251 is selected by a predetermined point operation (for example, a double click), the display control unit 19 causes the display unit 15 to displays the image observation screen 100 on which the selected in-vivo image and images adjacent thereto are arranged in the main display area 103.

Modified Example 2-7

Figure 21:
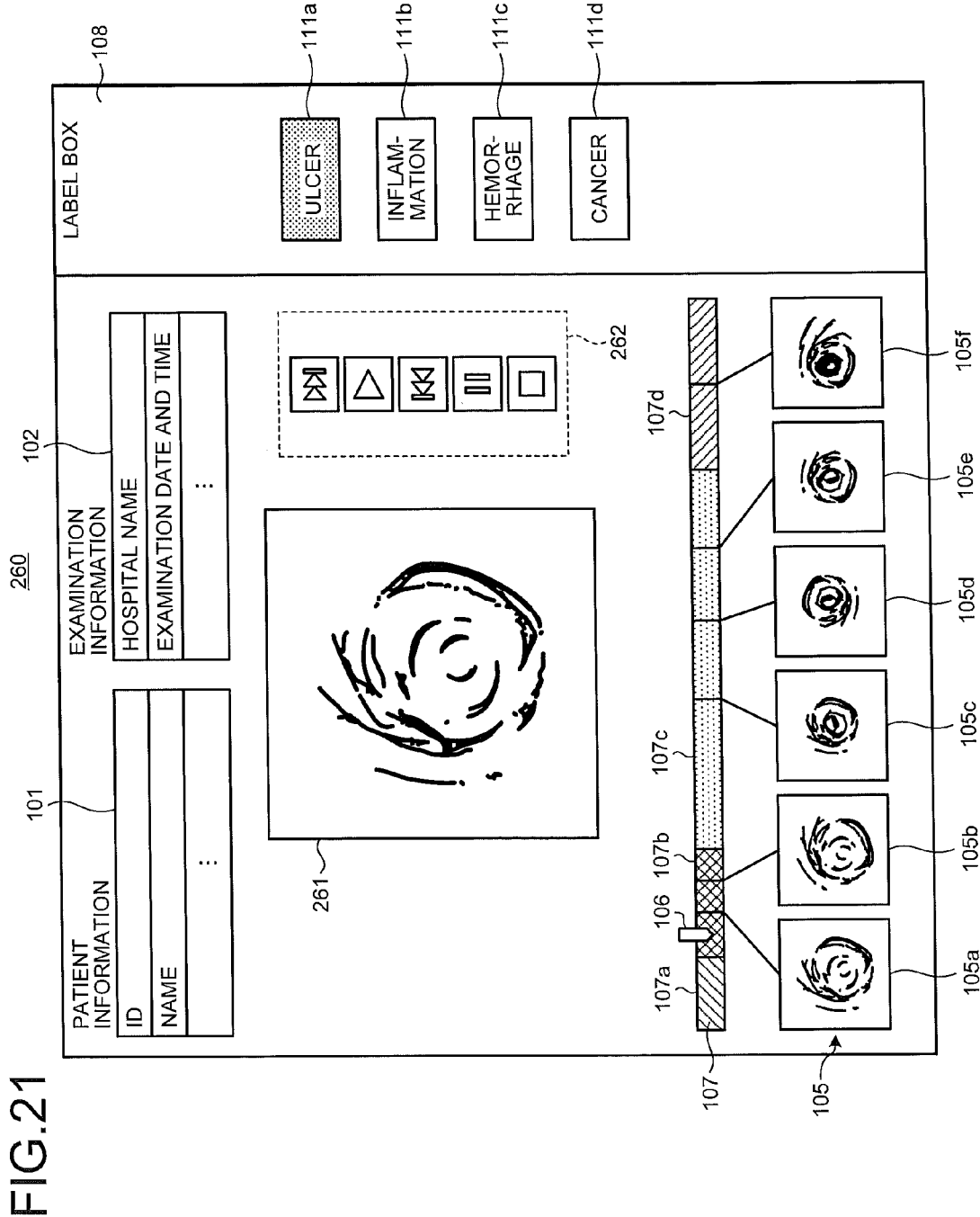
FIG. 21 is a schematic diagram that illustrates a display example of an image observation screen for a moving image according to Modified Example 2-7.

FIG. 21 is a schematic diagram that illustrates a display example of an image observation screen for a moving image. An image observation screen 260 illustrated in FIG. 21 includes: a patient information area 101 in which identification information of a subject 1 that is a patient is displayed; an examination information area 102 in which identification information of an examination that has been performed with respect to the subject 1 is displayed; a main display area 261 in which a moving image of in-vivo images is displayed; a group 262 of play operation buttons that receive input of a play operation for in-vivo images that are displayed in the main display area 261 as a moving image; a thumbnail area 105 in which captured images of the moving image that is mainly displayed are displayed on a reduced scale as thumbnails; and a label box display area 108 in which icons 111a to 111d that correspond to lesion labels are displayed.

On the image observation screen 260 for a moving image also, the in-vivo images are able to be processed per lesion label. For example, on the image observation screen 260, if any of the icons 111a to 111d in the label box display area 108 is selected by a predetermined pointer operation (for example, a double click), the label assigned image extracting unit 23 extracts, from the storage unit 14, in-vivo images to which a lesion label corresponding to the selected icon has been assigned. In addition, the display control unit 19 causes the display unit 15 to display the extracted in-vivo images by moving image display or frame-by-frame playback display (slide show) in the main display area 261. For example, in the case illustrated in FIG. 21, a state is illustrated in which the icon 111a representing ulcer is selected, and in-vivo images to which the ulcer label has been assigned are displayed by frame-by-frame playback display.

Alternatively, by a pointer operation on a screen, if another icon is additionally selected while any of the icons 111a to 111d in the label box display area 108 has already been selected, the label assigned image extracting unit 23 additionally extracts in-vivo images which correspond to the newly-selected icon. Moreover, the display control unit 19 causes the display unit 15 to additionally display the newly-extracted in-vivo images subsequently to the in-vivo images that are currently displayed in the main display area 261.

Modified Example 2-8

The collective process for the group of in-vivo images for each lesion label may be performed on a screen other than the image observation screen. For example, on the report creation screen 160 illustrated in FIG. 12, a process such as: displaying as a list the reduced images of the in-vivo images to which the corresponding lesion label has been assigned by selecting the icons 163a to 163d; and adding comments collectively to the in-vivo images to which the same lesion label has been assigned by operating the icons 163a to 163d, may be performed.

Modified Example 2-9

In the second embodiment described above, although the process for a series of in-vivo images that are obtained in one examination has been described, management with respect to: in-vivo images obtained in a plurality of examinations performed with respect to one patient; or in-vivo images obtained in examinations performed with respect to a plurality of patients, may be carried out.

Figure 22:
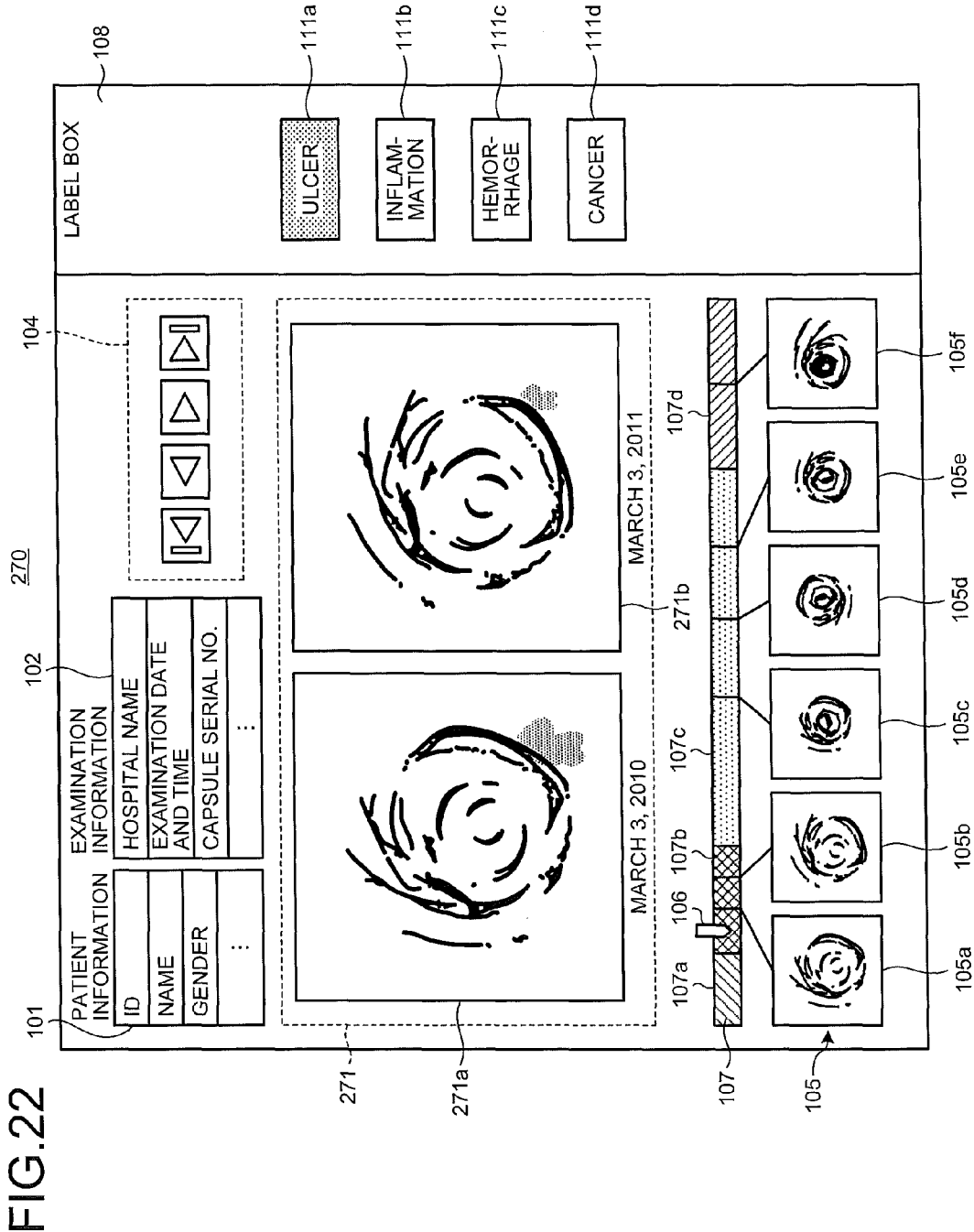
FIG. 22 is a schematic diagram that illustrates a display example of a progress observation screen according to Modified Example 2-9.

FIG. 22 is a display example of a progress observation screen that represents comparison of results of examinations that are performed for one patient at different times. In a main display area 271 of a progress observation screen 270 illustrated in FIG. 22, an in-vivo image obtained in the previous examination and an in-vivo image obtained in the latest examination are displayed side by side. When any of icons 111a to 111d in the label box display area 108 is selected by a pointer operation performed on the progress observation screen 270, the label assigned image extracting unit 23 extracts in-vivo images, to which a lesion label corresponding to the selected icon has been assigned, respectively from the in-vivo images obtained in the previous examination and the in-vivo images obtained in the latest examination. In addition, the display control unit 19 causes the display unit 15 to display the extracted in-vivo images in the main display area 271 side by side. For example, FIG. 22 illustrates a state in which an in-vivo images 271a (examination date: Mar. 3, 2010) and an in-vivo images 271b (examination date: Mar. 3, 2011) to which ulcer label has been assigned are displayed.

Modified Example 2-10

Figure 23:
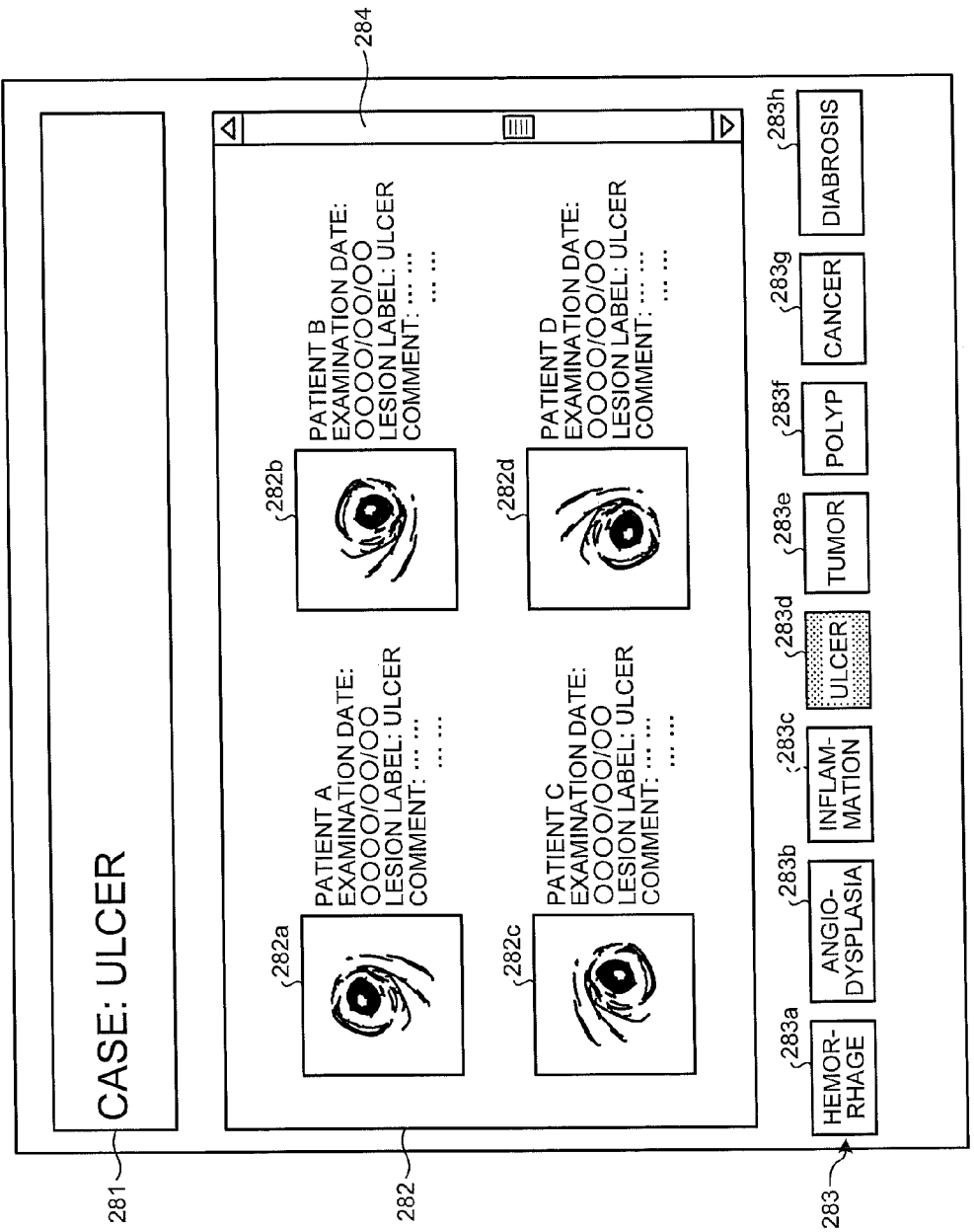
FIG. 23 is a schematic diagram that illustrates a display example of an atlas screen according to Modified Example 2-10.

FIG. 23 is a display example of an atlas screen on which results of examinations performed with respect to a plurality of patients are represented as case records. An atlas screen 280 illustrated in FIG. 23 includes: a title display area 281 in which information such as a case name is written; a case display area 282 in which case images 282a to 282d and related information are displayed; and a label box display area 283 in which icons 283a to 283h corresponding to lesion labels are displayed. Of these, in the case display area 282, a scroll key 284 is provided.

When any of the icons 283a to 283h in the label box display area 283 is selected by a pointer operation on the atlas screen 280, the label assigned image extracting unit 23 extracts in-vivo images, to which a lesion label corresponding to the selected icon has been assigned, from the results (groups of in-vivo images) of examinations performed with respect to a plurality of patients. In addition, the display control unit 19 causes the display unit 15 to display the extracted in-vivo images in the case display area 282 together with the related information such as patient names and examination dates and comments inserted into each in-vivo image. For example, FIG. 23 illustrates a case in which the icon 283d representing ulcer is selected, and in-vivo images to which the ulcer label has been assigned are displayed.

Third Embodiment

Next, a third embodiment of the present invention will be described.

A configuration of an image management apparatus according to the third embodiment is similar to that illustrated in FIG. 2, and different from the first embodiment in that, upon a label extracting unit 18 extracting a lesion label, priority levels are assigned to lesion labels in accordance with feature quantities of in-vivo images.

In this third embodiment, the label extracting unit 18 obtains a trend of a lesion of a series of in-vivo images as a whole based on feature quantities that are stored in the feature quantity storing unit 14b and assigns priority levels to lesion labels in accordance with that trend. For example, if a predetermined number or more or a predetermined ratio (for example, an average of general cases) or more of in-vivo images having strong red colors are included, the priority levels of the hemorrhage label and the angiodysplasia label are made higher. In addition, if a predetermined number or more or a predetermined ratio or more of in-vivo images having strong white colors are included, the priority level of encroachment label is made higher.

The display control unit 19 causes the display unit 15 to display icons that correspond to each lesion label within the label box display area in accordance with the priority levels assigned by the label extracting unit 18.

Figure 24:
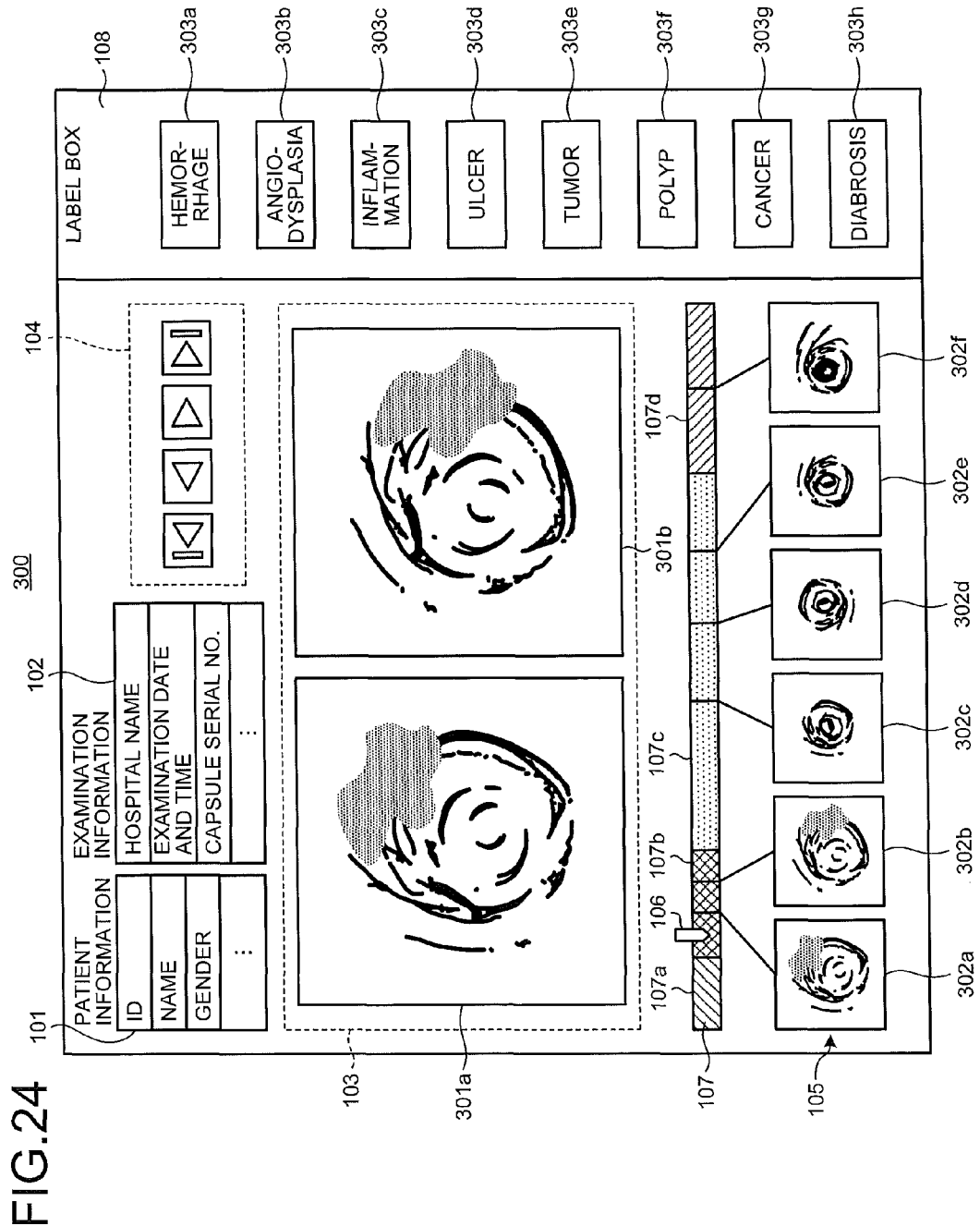
FIG. 24 is a schematic diagram that illustrates a display example of an image observation screen according to a third embodiment of the invention.

FIG. 24 is a schematic diagram that illustrates a display example of an image observation screen. A group of in-vivo images displayed on an image observation screen 300 illustrated in FIG. 24, as illustrated by in-vivo images 301a and 301b in the main display area 103 or reduced images 302a to 302f in the thumbnail area 105, include a number of in-vivo images each having a high proportion of a red-area. Accordingly, in the label box display area 108, of icons 303a to 303h, the icon 303a representing hemorrhage and the icon 303b representing angiodysplasia, which have high priority levels, are displayed from the top of the screen in accordance with the priority levels. The form of the priority display of icons is not limited to the form of arranging from the top in accordance with priority levels, and for example, the color, the shape, or the size of icons having higher priority levels may be made different from that of the other icons, or icons having higher priority levels may be arranged near the main display area 103 or the thumbnail area 105 so as to increase the ease of operation.

Modified Example 3-1

In the third embodiment described above, although all the icons are arranged in the label box display area 108 in accordance with the priority levels of the lesion labels, icons corresponding to lesions that are extracted in accordance with an organ of a selected in-vivo image may be displayed in accordance with the priority levels.

Fourth Embodiment

Next, a fourth embodiment of the present invention will be described.

Figure 25:
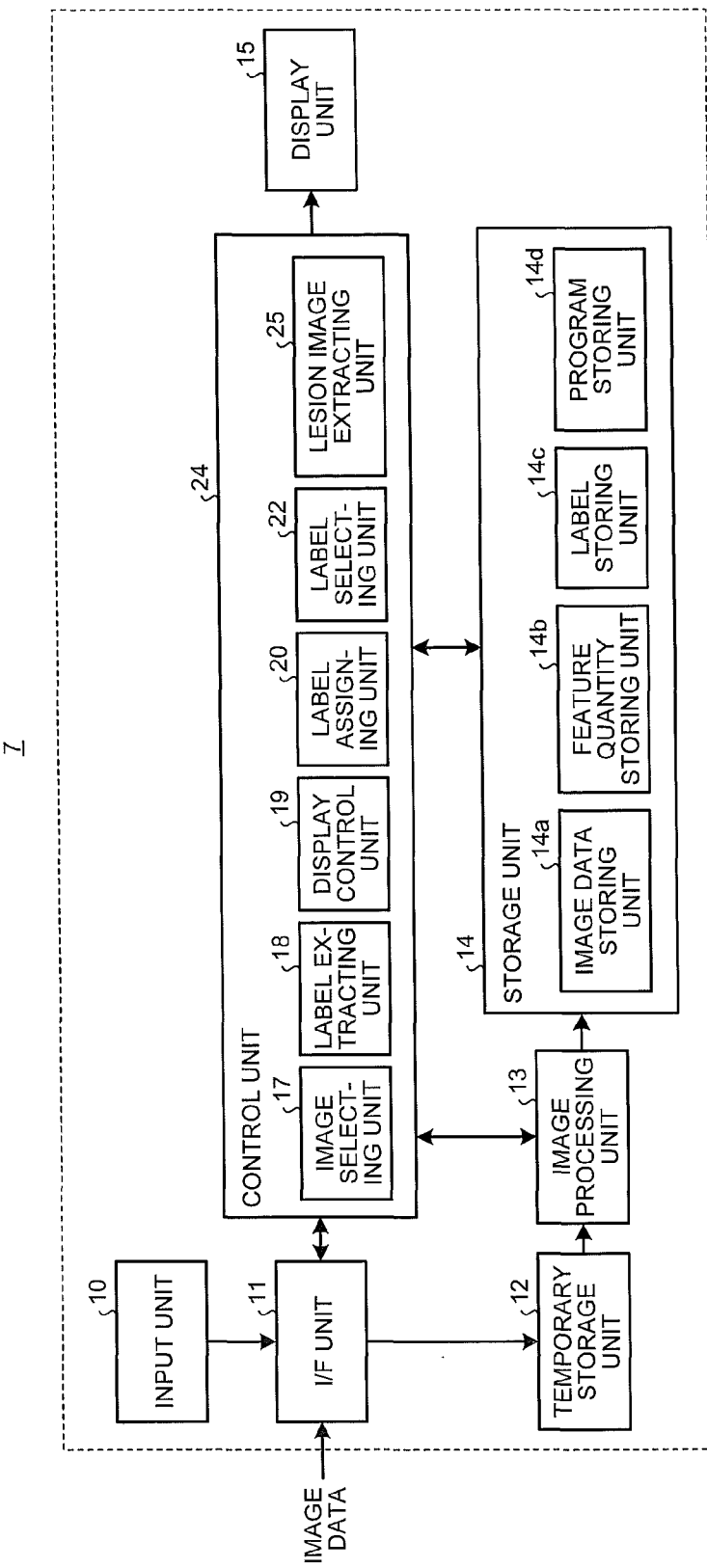
FIG. 25 is a block diagram that illustrates a configuration of an image management apparatus according to a fourth embodiment of the invention.

FIG. 25 is a block diagram that illustrates a configuration of an image management apparatus according to the fourth embodiment. As illustrated in FIG. 25, an image management apparatus 7 according to the fourth embodiment includes a control unit 24 that includes a lesion image extracting unit 25 instead of the label assigned image extracting unit 23 in the configuration of the control unit 21 illustrated in FIG. 13. The lesion image extracting unit 25 extracts in-vivo images that possibly correspond to a lesion label that is selected by the label selecting unit 22 based on the feature quantity of each in-vivo image that is stored in the storage unit 14. Further, in the fourth embodiment, the label storing unit 14c stores feature quantity information of in-vivo images corresponding to each lesion label. The rest of the configuration is similar to that illustrated in FIG. 13.

Figure 26:
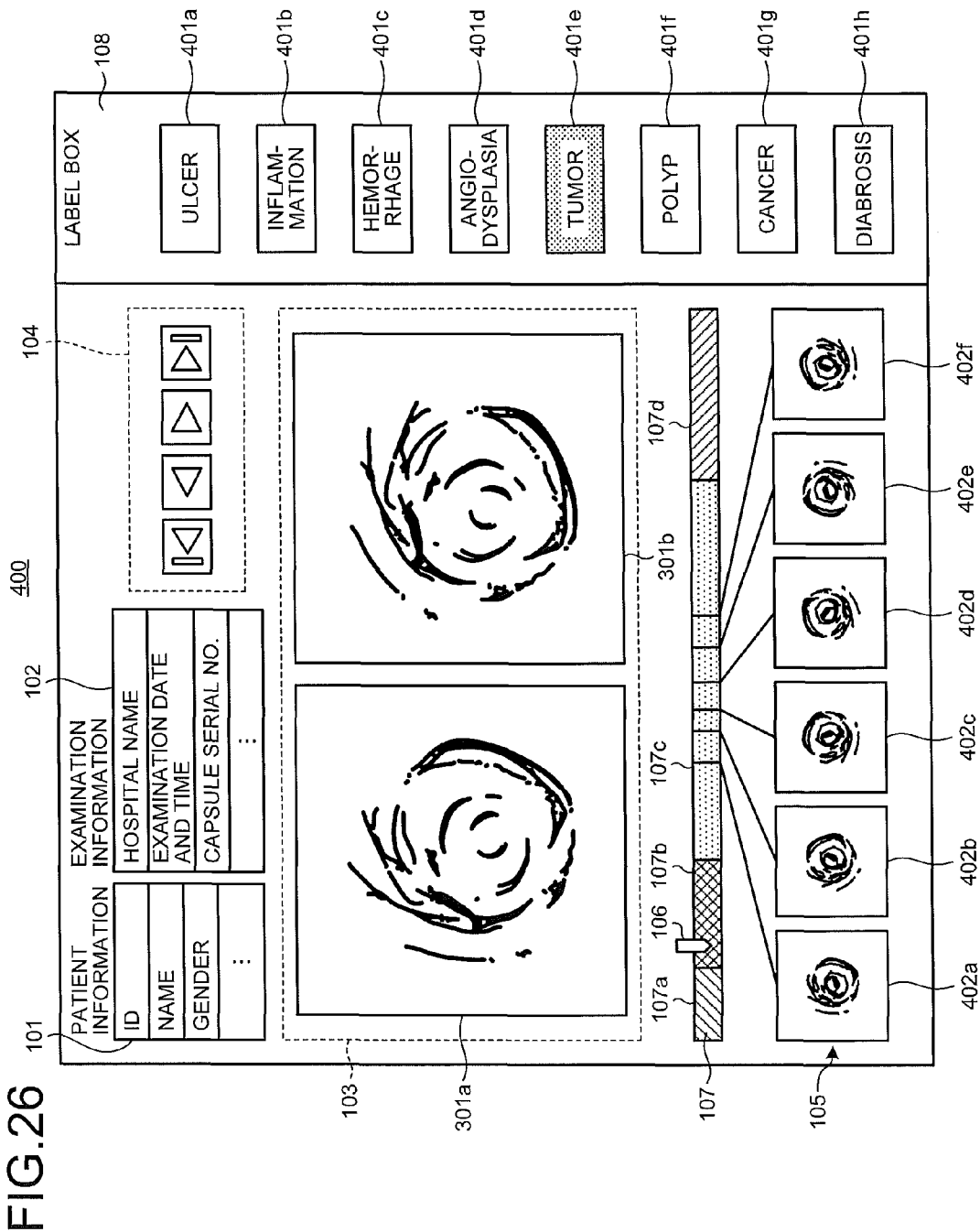
FIG. 26 is a schematic diagram that illustrates a display example of an image observation screen according to the fourth embodiment.

FIG. 26 is a schematic diagram that illustrates a display example of an image observation screen. On an image observation screen 400 illustrated in FIG. 26, icons 401a to 401h that correspond to labels stored in the label storing unit 14c are displayed in the label box display area 108.

When any of the icons 401a to 401h is selected by a pointer operation performed on the image observation screen 400, the label selecting unit 22 selects a lesion label that corresponds to the selected icon. Accordingly, the lesion image extracting unit 25 obtains feature quantity information corresponding to the selected lesion label from the label storing unit 14c. In addition, the lesion image extracting unit 25 obtains the feature quantity of each in-vivo image that is stored in the feature quantity storing unit 14b and extracts in-vivo images corresponding to the lesion label by referring to the feature quantity information of the selected lesion label. Furthermore, the display control unit 19 causes the display unit 15 to display reduced images corresponding to the in-vivo images extracted by the lesion image extracting unit 25 in the thumbnail area 105.

For example, FIG. 26 illustrates a state in which the icon 401e representing tumor is selected, and reduced images 402a to 402f that correspond to in-vivo images that match the feature quantity information of the tumor are displayed in the thumbnail area 105. The user is able to check whether or not the extracted in-vivo images actually correspond to the lesion by directly observing the reduced images 402a to 402f or by displaying the corresponding in-vivo images in the main display area 103 and observing the displayed in-vivo images.

Further, if the reduced images 402a to 402f (or the in-vivo images displayed in the main display area 103) and the selected icon are associated with each other through a pointer operation performed on the screen, the assignment of the lesion label to the extracted in-vivo images is finalized.

As described above, according to the fourth embodiment, a user just needs to check whether or not the in-vivo image extracted in correspondence with each lesion label corresponds to the lesion, and thus labor for observing all of the in-vivo images is able to be saved and efficiency of an image observation operation is able to be improved.

The embodiments and the modified examples described above are merely examples for implementing the present invention, and the present invention is not limited thereto.

The present invention may be variously modified in accordance with specifications or the like, and it is apparent from the above description that other various embodiments are further possible within the scope of the present invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image management apparatus comprising:
   a storage unit that stores a plurality of types of additional information assigned to a plurality of images;
   a calculation unit that calculates a feature quantity of each of the plurality of images;
   an additional information extracting unit that extracts, based on the feature quantity, one or more types of additional information of the plurality of types of additional information;
   a display control unit that generates one or more icons corresponding to the one or more types of additional information and causes the generated icons to be displayed on a screen;
   an input unit that receives input of a signal according to a user's operation;
   an image selecting unit that selects, from the plurality of images, an image according to the signal received by the input unit; and
   an additional information assigning unit that assigns to the selected image, when input of an operation signal associating the image selected by the image selecting unit with an icon selected from the one or more icons by the user is received by the input unit, additional information corresponding to the icon associated with the selected image, wherein:
   the plurality of types of additional information stored in the storage unit are different labels assignable by the user to the plurality of images,
   the additional information extracting unit extracts, based on the feature quantity calculated by the calculation unit for an image selected from the plurality of images, one or more of the different labels for the image selected from the plurality of images,
   the display control unit generates one or more icons respectively corresponding to the one or more of the labels extracted and causes the generated icons to be displayed on the screen for the image selected from the plurality of images, and
   the additional information assigning unit assigns to the selected image, when the input of the operation signal associating the selected image with an icon selected by the user from the one or more icons is received by the input unit, the label corresponding to the selected icon.

2. The image management apparatus according to claim 1, wherein the additional information extracting unit extracts the one or more types of additional information for each of groups into which the plurality of images are classified based on the feature quantities.

3. The image management apparatus according to claim 2, wherein the images are medical images and the groups are organ groups.

4. The image management apparatus according to claim 3, wherein
   the display control unit causes a bar indicating an index of time or space corresponding to the plurality of images and a slider specifying a point on the bar to be displayed on the screen, and
   the additional information extracting unit extracts the one or more types of additional information according to the organ group at a time or space corresponding to the point specified by the slider.

5. The image management apparatus according to claim 1, wherein the additional information extracting unit extracts the one or more types of additional information corresponding to the feature quantity of the image selected by the image selecting unit.

6. The image management apparatus according to claim 1, wherein the display control unit causes the one or more icons to be displayed on the screen in a format according to a frequency at which the corresponding additional information has been assigned.

7. The image management apparatus according to claim 1, wherein the display control unit causes the one or more icons to be displayed on the screen in a format according to the feature quantities of the plurality of images.

8. The image management apparatus according to claim 1, wherein the display control unit causes the additional information assigned to the selected image to be displayed on the screen in association with the image.

9. The image management apparatus according to claim 1, further comprising:
   an additional information selecting unit that selects, from the one or more icons displayed on the screen, additional information corresponding to an icon selected according to a signal received by the input unit; and
   an image extracting unit that extracts, from the plurality of images, an image to which the additional information selected by the additional information selecting unit has been assigned.

10. The image management apparatus according to claim 1, wherein the images are medical images and the additional information is a lesion label corresponding to a lesion captured in the medical image.

11. The image management apparatus according to claim 1, wherein the display control unit causes the additional information that has been assigned to the selected image to be displayed on the screen beside a thumbnail image of the image.

12. An operating method of an image management apparatus, comprising:
   calculating, by a calculation unit, a feature quantity of each of a plurality of images;
   extracting, by an additional information extracting unit, from a plurality of types of additional information to be assigned to the plurality of images and stored beforehand in a storage unit, one or more types of additional information, based on the feature quantity;
   generating and displaying, by a display control unit, on a screen one or more icons corresponding to the one or more types of additional information;
   receiving, by an input unit, input of a signal according to a user's operation;
   selecting, by an image selecting unit, from the plurality of images, an image according to the signal received via the input; and
   assigning to the selected image, by an additional information assigning unit, when input of an operation signal associating the image selected in the selecting of the image with an icon selected from the one or more icons by the user is received, additional information corresponding to the icon associated with the image,
wherein:
   the plurality of types of additional information stored are different labels assignable by the user to the plurality of images,
   one or more of the different labels for an image selected from the plurality of images are extracted, based on the feature quantity calculated for the image selected from the plurality of images,
   one or more icons respectively corresponding to the one or more of the labels extracted are generated and caused to be displayed on the screen for the image selected from the plurality of images, and
   when the input of the operation signal associating the selected image with an icon selected by the user from the one or more icons is received, the label corresponding to the selected icon is assigned to the selected image.

13. A non-transitory computer-readable recording medium on which an executable program is recorded, the program instructing a processor to perform:
   calculating a feature quantity of each of a plurality of images;
   extracting, from a plurality of types of additional information to be assigned to the plurality of images and stored beforehand in a storage unit, one or more types of additional information, based on the feature quantity;
   generating and displaying on a screen one or more icons corresponding to the one or more types of additional information;
   receiving input of a signal according to a user's operation;
   selecting, from the plurality of images, an image according to the signal received via the input; and
   assigning to the selected image, when input of an operation signal associating the image selected in the selecting of the image with an icon selected from the one or more icons by the user is received, additional information corresponding to the icon associated with the image,
wherein:
   the plurality of types of additional information stored are different labels assignable by the user to the plurality of images,
   one or more of the different labels for an image selected from the plurality of images are extracted, based on the feature quantity calculated for the image selected from the plurality of images,
   one or more icons respectively corresponding to the one or more of the labels extracted are generated and caused to be displayed on the screen for the image selected from the plurality of images, and
   when the input of the operation signal associating the selected image with an icon selected by the user from the one or more icons is received, the label corresponding to the selected icon is assigned to the selected image.

14. A capsule endoscope system comprising:
   a capsule endoscope that is introduced inside a body of a subject, performs imaging, and generates image data corresponding to in-vivo images of the subject;
   a receiving device that receives the image data generated by the capsule endoscope via wireless communications with the capsule endoscope; and
   an image management apparatus that receives and manages the image data received by the receiving device, wherein the image management apparatus includes:
      a storage unit that stores a plurality of types of additional information assigned to a plurality of images;
      a calculation unit that calculates a feature quantity of each of the plurality of images;
      an additional information extracting unit that extracts, based on the feature quantity, one or more types of additional information of the plurality of types of additional information;
      a display control unit that generates one or more icons corresponding to the one or more types of additional information and causes the generated icons to be displayed on a screen;
      an input unit that receives input of a signal according to a user's operation;
      an image selecting unit that selects, from the plurality of images, an image according to the signal received by the input unit; and
      an additional information assigning unit that assigns to the selected image, when input of an operation signal associating the image selected by the image selecting unit with an icon selected from the one or more icons by the user is received by the input unit, additional information corresponding to the icon associated with the selected image,
wherein:
   the plurality of types of additional information stored in the storage unit are different labels assignable by the user to the plurality of images,
   the additional information extracting unit extracts, based on the feature quantity calculated by the calculation unit for an image selected from the plurality of images, one or more of the different labels for the image selected from the plurality of images,
   the display control unit generates one or more icons respectively corresponding to the one or more of the labels extracted and causes the generated icons to be displayed on the screen for the image selected from the plurality of images, and the additional information assigning unit assigns to the selected image, when the input of the operation signal associating the selected image with an icon selected by the user from the one or more icons is received by the input unit, the label corresponding to the selected icon.

* * * * *